US010934541B2

(12) United States Patent
Okajima et al.

(10) Patent No.: US 10,934,541 B2
(45) Date of Patent: Mar. 2, 2021

(54) METHOD FOR SEPARATING NUCLEIC ACID FROM SPECIMEN CONTAINING NUCLEIC ACID AND DEVICE THEREFOR

(71) Applicant: Kaneka Corporation, Osaka (JP)

(72) Inventors: Motonori Okajima, Hyogo (JP); Takashi Nishizono, Hyogo (JP); Shigehiko Miyamoto, Hyogo (JP); Hozumi Tanaka, Hyogo (JP)

(73) Assignee: KANEKA CORPORATION, Osaka (JP)

(*) Notice: Subject to any disclaimer, the term of this patent is extended or adjusted under 35 U.S.C. 154(b) by 227 days.

(21) Appl. No.: 15/917,010

(22) Filed: Mar. 9, 2018

(65) Prior Publication Data

US 2018/0201922 A1    Jul. 19, 2018

Related U.S. Application Data

(63) Continuation-in-part of application No. PCT/JP2016/076692, filed on Sep. 9, 2016.

(30) Foreign Application Priority Data

Sep. 10, 2015    (JP) ............................. JP2015-178442

(51) Int. Cl.
*C12N 15/10* (2006.01)
*C12M 1/26* (2006.01)
(Continued)

(52) U.S. Cl.
CPC ............ *C12N 15/1006* (2013.01); *C12M 1/00* (2013.01); *C12M 1/26* (2013.01); *C12N 15/00* (2013.01); *C12Q 1/24* (2013.01); *G01N 2333/35* (2013.01)

(58) Field of Classification Search
CPC ................. C12N 15/1006; C12N 15/1003; C12N 15/10; C12N 15/09; C12M 1/00; C12M 1/26
(Continued)

(56) References Cited

U.S. PATENT DOCUMENTS 5,234,809 A    8/1993   Boom et al.
7,727,718 B2 *  6/2010   Chomczynski ...... C12Q 1/6806
                                                    435/173.7
(Continued)

FOREIGN PATENT DOCUMENTS

JP    2001-78790 A    3/2001
JP    2004-500067 A   1/2004
(Continued)

OTHER PUBLICATIONS

Qiagen, User-Developed Protocol: Purification of total DNA from viscous samples using the DNeasy® Blood & Tissue Kit with acetyl cysteine (NALC) pretreatment, 2006, pp. 1-3. (Year: 2006).*
(Continued)

*Primary Examiner* — Christine T Mui
(74) *Attorney, Agent, or Firm* — Osha Bergman Watanabe & Burton

(57) ABSTRACT

A method for separating a nucleic acid from a specimen includes accommodating a specimen in an accommodation space provided in a nucleic acid-collecting member, transferring a treatment reagent to the nucleic acid-collecting member by connecting a treatment reagent-accommodating container to a treatment reagent-supplying opening of the nucleic acid-collecting member, obtaining a mixture by mixing the specimen and the treatment reagent in a mixing space formed by combining an inner container space of the treatment reagent-accommodating container and the accommodation space of the nucleic acid-collecting member, and pressure-feeding the mixture by reducing a volume of the
(Continued)

inner container space of the treatment reagent-accommodating container and discharging the mixture from an mixture-discharging opening of the nucleic acid-collecting member via a carrier that adsorbs the nucleic acid released in the mixture while allowing the mixture to permeate therethrough.

4 Claims, 10 Drawing Sheets

Specification includes a Sequence Listing.

(51) Int. Cl.
*C12M 1/00* (2006.01)
*C12N 15/00* (2006.01)
*C12Q 1/24* (2006.01)

(58) Field of Classification Search
USPC .......................................................... 436/94
See application file for complete search history.

(56) References Cited

U.S. PATENT DOCUMENTS

| | | | |
|---|---|---|---|
| 2006/0051799 A1 | 3/2006 | Iwaki et al. | |
| 2006/0121516 A1* | 6/2006 | Norman | C07K 14/005 435/6.14 |
| 2006/0252085 A1* | 11/2006 | Pollner | C12Q 2527/101 435/6.12 |
| 2007/0009893 A1* | 1/2007 | Mori | C12N 15/1006 435/6.11 |
| 2007/0244314 A1 | 10/2007 | Mori | |
| 2008/0305482 A1* | 12/2008 | Brentano | C12Q 1/6865 435/6.18 |
| 2009/0306359 A1 | 12/2009 | Hillebrand et al. | |
| 2010/0035331 A1 | 2/2010 | Tsuchiya et al. | |
| 2011/0015379 A1 | 1/2011 | Mori et al. | |
| 2014/0058043 A1* | 2/2014 | Miyamoto | C12Q 1/6846 525/289 |
| 2014/0275510 A1* | 9/2014 | Gundling | C12N 15/1003 536/25.42 |
| 2014/0356860 A1 | 12/2014 | Flugge et al. | |

FOREIGN PATENT DOCUMENTS

| | | |
|---|---|---|
| JP | 2005-168449 A | 6/2005 |
| JP | 2006-6258 A | 1/2006 |
| JP | 2006-94857 A | 4/2006 |
| JP | 2009-100688 A | 5/2009 |
| JP | 2010-29126 A | 2/2010 |
| JP | 2010-158190 A | 7/2010 |
| JP | 2011-177045 A | 9/2011 |
| JP | 2014-526255 A | 10/2014 |
| WO | 01/46404 A1 | 6/2001 |
| WO | 2007/094506 A1 | 8/2007 |
| WO | 2009/060847 A1 | 5/2009 |
| WO | 2010075116 A2 | 7/2010 |
| WO | 2014/144209 A1 | 9/2014 |
| WO | 2014/182847 A1 | 11/2014 |
| WO | 2016183292 A1 | 11/2016 |

OTHER PUBLICATIONS

International Search Report issued in PCT/JP2016/076692; dated Dec. 13, 2016 (5 pages).
QIAprep Spin Miniprep Kit, "Quick-StartProtocol Sample & Assay Technologies," Oct. 1, 2010, XP055578937, Retrieved from the Internet: URL: http://2014.igem.org/wiki/images/f/f5/QIAprep-Spin-Miniprep-Kit-EN.pdf (2 pages).
Schoeman et al., "A comparison of four sputum pre-extraction preparation methods for identifying and characterising *Mycobacterium tuberculosis* using GCxGC-TOFMS metabolomics," Journal of Microbiological Methods, vol. 91, No. 2, Sep. 8, 2012, pp. 301-311, XP028951431 (11 pages).
Extended European Search Report issued in corresponding European Application No. 16844510.4; dated Apr. 16, 2019 (8 pages).
Office Action issued in corresponding European Application No. 16844510.4, dated Apr. 23, 2020 (7 pages).

* cited by examiner

METHOD FOR SEPARATING NUCLEIC ACID FROM SPECIMEN CONTAINING NUCLEIC ACID AND DEVICE THEREFOR

This application is a continuation-in-part of PCT International Application PCT/JP2016/076692 filed Sep. 9, 2016, which in turns claims benefit of Japanese Patent Application No. 2015-178442, the entire contents of each of which is incorporated herein by reference.

TECHNICAL FIELD

The present invention relates to a method for separating a nucleic acid from a specimen containing a nucleic acid such as a biological sample. The present invention further relates to a device for separating a nucleic acid from a specimen containing a nucleic acid.

BACKGROUND ART

Genetic tests, by which it is possible to determine results by nucleic acid analysis with high sensitivity within a short period of time, are industrially important tests that can be applied to various fields of medicine, agriculture, livestock raising, fishery, quality inspection, and the like. For genetic tests, it is necessary to elute and purify nucleic acids from specimens. The most widely used nucleic acid purification method is the bind-elute method, to which a characteristic that a nucleic acid binds to a nucleic acid adsorptive carrier in the presence of a chaotropic agent is applied (Patent Literature 1 and 2). The above purification method comprises: (a) dissolution step: dissolution of a specimen and elution of a nucleic acid; (b) adsorption step: binding of a nucleic acid adsorptive carrier and the nucleic acid; (c) washing step: washing of the nucleic acid bound to the nucleic acid adsorptive carrier; and (d) elution step: elution of the nucleic acid. In particular, a combination of the method and a spin column is an excellent method, by which high-purity nucleic acids can be purified.

However, the above method requires skilled researchers to work in a fully equipped laboratory or the like using laboratory equipment including a centrifuge, a micropipette, a vortex mixer, and an incubator with highly advanced techniques. In the fields of medicine, agriculture, livestock raising, fishery, food, and the like where there is a demand for genetic tests, some facilities lack skilled human resources and equipment, which are necessary. In fact, such facilities have to outsource genetic tests, which basically enables determination of results in a short period of time, to external institutions, although outsourcing is time- and cost-consuming. Rapid determination of results, which is a feature of genetic tests, has not been fully utilized in practice.

In addition, specimens to be examined by genetic tests are often pathogenic organisms such as viruses and bacteria. The risk of infection in those conducting the tests is always a problematic issue. Most of genetic tests require the use of equipment and facility corresponding to the bio safety level. The use of such equipment and facility is a very complicated procedure, compared with the case in which the use thereof is not required. In fact, the procedure places a huge burden on those who conduct the tests.

Patent Literature 3 discloses a method in which a nucleic acid extraction liquid containing a nucleic acid eluted from a specimen is brought into contact with zeolite such that zeolite adsorbs unnecessary components, thereby purifying the nucleic acid. However, this method fails to concentrate and purify a nucleic acid as in the case of the bind-elute method. The method depends on the nucleic acid concentration in a specimen, which is problematic. In addition, impurities that can be removed by adsorption are limited. The degree of purification is inferior to that of the bind-elute method. Therefore, the technology level of the method is insufficient to replace the bind-elute method.

Patent Literature 4 discloses a pretreatment method for detecting the gene of an acid-fast bacterium contained in sputum. This method is intended to separate cells of an acid-fast bacterium from a sputum but not to extract the gene (nucleic acid) from sputum.

Patent Literature 5 discloses a method for separating and purifying a nucleic acid using a nucleic acid-adsorptive porous membrane, which is appropriate for automation and downsizing. The method of Patent Literature 5 is characterized in that a porous membrane which adsorbs a nucleic acid via interaction that does not substantially involve ion binding is used as a nucleic acid-adsorptive porous membrane. The method of Patent Literature 5 also fails to solve the problem of the conventional bind-elute method.

Patent Literature 6 discloses a composition of a chaotropic agent that allows a nucleic acid in liquid to be adsorbed by a solid-phase carrier. However, Patent Literature 6 also fails to disclose means for solving the problem of the conventional bind-elute method.

CITATION LIST

Patent Literature

Patent Literature 1: JP Patent Publication (Kokai) No. 2001-78790 A

Patent Literature 2: JP Patent Publication (Kohyo) No. 2014-526255 A

Patent Literature 3: International Publication WO2009/060847

Patent Literature 4: JP Patent Publication (Kokai) No. 2009-100688 A

Patent Literature 5: JP Patent Publication (Kokai) No. 2005-168449 A

Patent Literature 6: U.S. Patent Publication No. 2009/0306359

SUMMARY OF INVENTION

Technical Problem

An object of the present invention is to provide a method for efficiently separating a nucleic acid from a specimen containing a nucleic acid, a device therefor, and a reagent therefor.

Solution to Problem

According to the present invention, the following inventions are provided as means for achieving the above object.

The following is provided according to the present invention: a method for separating a nucleic acid from a specimen containing a nucleic acid by bringing a mixture of a specimen containing a nucleic acid and a treatment reagent for causing a nucleic acid in a specimen to be released into contact with a carrier that adsorbs a nucleic acid, wherein a device is used, the device comprising:

a treatment reagent-accommodating container configured to have an inner container space, the volume of which can be reduced, the container accommodating a treatment reagent for causing a nucleic acid in a specimen to be released in the inner container space and having a discharging opening for releasing the treatment reagent;

a nucleic acid-collecting member configured to have an accommodation space for accommodating a specimen, in which a treatment reagent-supplying opening is formed on one side of the accommodation space so as to be connected to the treatment reagent-accommodating container, thereby allowing the treatment reagent to be supplied, and a mixture-discharging opening is formed on the other side of the accommodation space so as to discharge the mixture via a carrier that adsorbs a nucleic acid released in the mixture while allowing the mixture to permeate therethrough, and the treatment reagent-accommodating container further comprising a cover for sealing the discharging opening attached to the discharging opening; and the device is configured such that the nucleic acid-collecting member allows the discharging opening sealed with the cover to be opened, thereby causing the discharging opening to be communicated with the treatment reagent-supplying opening, when the treatment reagent-accommodating container is connected to the treatment reagent-supplying opening of the nucleic acid-collecting member, and wherein the method comprises:

step 1 of accommodating a specimen in the accommodation space of the nucleic acid-collecting member;

step 2 of connecting the treatment reagent-accommodating container to the treatment reagent-supplying opening of the nucleic acid-collecting member, thereby causing the discharging opening to be communicated with the treatment reagent-supplying opening, following step 1;

step 3 of mixing the specimen and the treatment reagent to obtain the mixture in a mixing space formed by combining the inner container space of the treatment reagent-accommodating container and the accommodation space of the nucleic acid-collecting member in step 2 and allowing a nucleic acid contained in the specimen to be released in the mixture; and step 4 of pressure-feeding the mixture containing the nucleic acid released in step 3 by reducing a volume of the inner container space of the treatment reagent-accommodating container and discharging the mixture from the mixture-discharging opening of the nucleic acid-collecting member via the carrier.

A device used for the method of the present invention has features of the device described below.

The method of the present invention preferably further comprises step 5 of washing the carrier using a washing liquid, thereby removing unnecessary components other than a nucleic acid from the carrier, following step 4.

The method of the present invention preferably further comprises step 6 of bringing an eluent for eluting a nucleic acid into contact with the carrier, thereby eluting the nucleic acid from the carrier, following step 5.

In the method of the present invention, the treatment reagent preferably contains a component for reducing infectivity of a microorganism and a component for causing a nucleic acid to be released.

The following is also provided according to the present invention: a device for separating a nucleic acid from a specimen containing a nucleic acid by bringing a mixture of a specimen containing a nucleic acid and a treatment reagent for causing a nucleic acid in a specimen to be released into contact with a carrier that adsorbs a nucleic acid, which comprises: a treatment reagent-accommodating container configured to have an inner container space, the volume of which can be reduced, the container accommodating a treatment reagent for causing a nucleic acid in a specimen to be released in the inner container space and having a discharging opening for releasing the treatment reagent; and a nucleic acid-collecting member configured to have an accommodation space for accommodating a specimen, in which a treatment reagent-supplying opening is formed on one side of the accommodation space so as to be connected to the treatment reagent-accommodating container, thereby allowing the treatment reagent to be supplied, and a mixture-discharging opening is formed on the other side of the accommodation space so as to discharge the mixture via a carrier that adsorbs a nucleic acid released in the mixture while allowing the mixture to permeate therethrough, wherein the device is configured such that a cover for sealing the discharging opening is attached to the discharging opening of the treatment reagent-accommodating container, and wherein the nucleic acid-collecting member allows the discharging opening sealed with the cover to be opened, thereby causing the discharging opening to be communicated with the treatment reagent-supplying opening, when the treatment reagent-accommodating container is connected to the treatment reagent-supplying opening of the nucleic acid-collecting member.

Herein, in a specific embodiment of the feature "the nucleic acid-collecting member allows the discharging opening sealed with the cover to be opened, thereby causing the discharging opening to be communicated with the treatment reagent-supplying opening, when the treatment reagent-accommodating container is connected to the treatment reagent-supplying opening of the nucleic acid-collecting member," the nucleic acid-collecting member comprises a portion that is pressed against the cover so as to break the cover when the treatment reagent-accommodating container is connected to the treatment reagent-supplying opening of the nucleic acid-collecting member. In this embodiment, as the cover is broken when the portion is pressed, a seal of the discharging opening with the cover is opened, and the discharging opening and the treatment reagent-supplying opening are communicated with each other. In one embodiment in which the nucleic acid-collecting member has a circumference wall portion surrounding the accommodation space, and a part of the circumference wall portion, which surrounds the circumference border of the treatment reagent-supplying opening, is a treatment reagent-supplying opening periphery portion, the end portion of the treatment reagent-supplying opening periphery portion is exemplified as the above-described portion. In this specific embodiment, the cover can be broken when the above portion of the nucleic acid-collecting member is pressed. Specifically, the cover is formed with a film.

Preferably, the device of the present invention is described as follows: the treatment reagent-accommodating container comprises a discharge opening periphery portion surrounding a circumference border of the discharging opening; the nucleic acid-collecting member comprises a peripheral wall portion surrounding the accommodation space, a part of the peripheral wall portion is a treatment reagent-supplying opening periphery portion surrounding a peripheral border of the treatment reagent-supplying opening; the treatment reagent-accommodating container and the nucleic acid-collecting member are configured to be connected to each other in a state in which an inner peripheral surface of the discharging opening periphery portion and an external peripheral surface of the treatment reagent-supplying opening periphery portion are in contact with each other; one end portion of the treatment reagent-supplying opening periphery portion of the nucleic acid-collecting member, which is positioned on the side of the treatment reagent-supplying opening, is configured such that when the treatment reagent-accommodating container and the nucleic acid-collecting member are connected to each other, the end portion breaks the cover of the treatment reagent-accommodating container.

Herein, in a specific embodiment of the feature "one end portion of the treatment reagent-supplying opening periphery portion of the nucleic acid-collecting member, which is positioned on the side of the treatment reagent-supplying opening, is configured such that when the treatment reagent-accommodating container and the nucleic acid-collecting member are connected to each other, the end portion breaks the cover of the treatment reagent-accommodating container," when the treatment reagent-supplying opening periphery portion of the nucleic acid-collecting member allows the treatment reagent-accommodating container and the nucleic acid-collecting member to be connected to each other on the side of the treatment reagent-supplying opening while the internal circumference surface of the discharging opening periphery portion and the external circumference surface of the treatment reagent-supplying opening periphery portion are brought into contact with each other, the end portion is pressed against the cover so as to break the cover. The cover can be broken when the end portion of the treatment reagent-supplying opening periphery portion is pressed. Specifically, the cover is formed with a film. In this specific embodiment, the end portion is preferably a sharp end portion.

In the device of the present invention, it is further preferable that the nucleic acid-collecting member further comprises a flange portion that extends outwardly from the external circumference surface of the circumference wall portion and a mixture leakage-preventing wall portion that stands on the circumference border of the flange portion toward a side of the circumference wall portion where the treatment reagent-supplying opening is formed, that at least one compressible and deformable ring-shaped protrusion that extends in a circumferential direction so as to surround the whole circumference and protrudes in a radial direction is formed on either one or both of the external circumference surface of the discharging opening periphery portion and the internal circumference surface of the mixture leakage-preventing wall portion, and that the treatment reagent-accommodating container and the nucleic acid-collecting member are formed such that when the treatment reagent-accommodating container and the nucleic acid-collecting member are connected to each other, the external circumference surface of the discharging opening periphery portion and the internal circumference surface of the mixture leakage-preventing wall portion face each other, thereby causing the ring-shaped protrusion flanked between the external circumference surface of the discharging opening periphery portion and the internal circumference surface of the mixture leakage-preventing wall portion to be compressed and deformed, which prevents the passage of the mixture present between the external circumference surface of the discharging opening periphery portion and the internal circumference surface of the mixture leakage-preventing wall portion and/or the passage of the mixture present between the external circumference surface of the treatment reagent-supplying opening periphery portion and the internal circumference surface of the discharging opening periphery portion.

The device of the present invention preferably further comprises a washing liquid-accommodating container accommodating a washing liquid for removing unnecessary components other than a nucleic acid from the carrier.

The device of the present invention preferably further comprises an eluent-accommodating container accommodating an eluent for eluting a nucleic acid from the carrier.

In the device of the present invention, the treatment reagent preferably contains a component for reducing infectivity of a microorganism and a component for causing a nucleic acid to be released.

According to the present invention, the following is further provided: a specimen treatment reagent for causing a nucleic acid in a specimen to be released, which comprises: a component for reducing infectivity of a microorganism that is at least one selected from the group consisting of an organic solvent, an aldehyde disinfectant, an iodine agent, a chlorine agent, peracetic acid, ozone, hydrogen peroxide, merbromin, 6,9-diamino-2-ethoxyacridine lactate, a surfactant, and an alkaline substance; and a component for causing a nucleic acid to be released that is at least one selected from the group consisting of an alkaline substance and a surfactant.

The specimen treatment reagent of the present invention further comprises a component for facilitating a carrier to adsorb a nucleic acid that is at least one selected from the group consisting of a chaotropic agent and an organic solvent.

The specimen treatment reagent of the present invention preferably further comprises a thiol reductant and more preferably comprises alcohol as the component for reducing infectivity of a microorganism and an alkaline substance as the component for causing a nucleic acid to be released.

The specimen treatment reagent of the present invention preferably further comprises a thiol reductant, the component for reducing infectivity of a microorganism, and the component for causing a nucleic acid to be released, and more preferably comprises alcohol as the component for reducing infectivity of a microorganism.

The specimen treatment reagent of the present invention is preferably a specimen treatment reagent for causing a nucleic acid in a specimen to be released and allowing the released nucleic acid to be adsorbed by a carrier containing silica.

According to the present invention, use of the specimen treatment reagent for causing a nucleic acid in a specimen to be released is also provided.

The use of the present invention is preferably the use of the specimen treatment reagent, for causing a nucleic acid in a specimen to be released and allowing the released nucleic acid to be adsorbed by a carrier containing silica.

According to the present invention, as another method of the present invention, a method for causing a nucleic acid in a specimen to be released, which comprises step 1 of mixing a specimen and the specimen treatment reagent to obtain a mixture, thereby reducing infectivity of a microorganism that is possibly contained the specimen in the mixture and causing a nucleic acid in the specimen to be released.

According to the present invention, as another method of the present invention, a method for separating a nucleic acid from a specimen, which comprises the above-described step 1; and step 2 of allowing a nucleic acid separated from the specimen to be adsorbed by a carrier in the presence of a mixture formed in the step 1, is provided.

According to the present invention, as another method of the present invention, a method for separating a nucleic acid from a specimen containing a nucleic acid and a component crosslinked by an S—S bond, which comprises allowing a nucleic acid separated from the specimen to be adsorbed by a carrier in the presence of a mixture of the specimen treatment reagent containing a thiol reductant and the specimen, is provided.

In another method of the present invention, the carrier is preferably a carrier containing silica.

In one embodiment of the method, device, reagent, or use of or another method of the present invention, a specimen containing a nucleic acid is sputum, preferably sputum containing an infectious microorganism or a nucleic acid from an infectious microorganism, and particularly preferably sputum containing an acid-fast bacterium (which is hereinafter preferably tuberculosis bacterium) or a nucleic acid from an acid-fast bacterium. In this embodiment, a nucleic acid to be separated is a nucleic acid contained in sputum, preferably a nucleic acid from an infectious microorganism or different cells (e.g., human cells or other animal cells in sputum), and particularly preferably a nucleic acid from an acid-fast bacterium. In the method, device, reagent, or use of or another method in the above embodiment, a treatment reagent to be used preferably contains a reductant for improving fluidity of sputum. Such reductant is preferably a thiol reductant and more preferably a cysteine reductant. A preferable cysteine reductant is at least one selected from among N-acetyl-L-cysteine, L-cysteine, L-cysteine ethyl ester, L-cysteine methyl ester, N-ethyl-L-cysteine, N-methyl-L-cysteine, and salts of these compounds. The salts are not particularly limited as long as they can function as a reductant, which may be in the form of a hydrogen halide salt (e.g., hydrochloride), an alkali metal salt (e.g., sodium salt), or the like. Examples thereof include a hydrochloride of L-cysteine ethyl ester and a hydrochloride of L-cysteine methyl ester. In addition, a treatment reagent to be used is preferably in the liquid form.

In one embodiment of the method, device, reagent, or use of or another method of the present invention, a specimen containing a nucleic acid is a specimen containing a nucleic acid from an acid-fast bacterium. In this embodiment, a nucleic acid to be separated is a nucleic acid from an acid-fast bacterium.

In another embodiment of the method, device, reagent, or use of or another method of the present invention, a specimen containing a nucleic acid is a specimen excluding sputum. Sputum to be excluded herein is sputum containing an infectious microorganism or a nucleic acid from an infectious microorganism and particularly preferably sputum containing an acid-fast bacterium or a nucleic acid from an acid-fast bacterium. In the method, device, reagent, or use of or another method of the present invention in the above embodiment, a treatment reagent to be used may not contain the reductant.

In another embodiment of the method, device, reagent, or use of or another method of the present invention, a specimen containing a nucleic acid is a specimen containing a nucleic acid other than a nucleic acid from an acid-fast bacterium. In this embodiment, a nucleic acid to be separated is a nucleic acid other than a nucleic acid from an acid-fast bacterium.

This description includes part or all of the content as disclosed in the description and/or drawings of Japanese Patent Application No. 2015-178442, which is a priority document of the present application.

Advantageous Effects of Invention

According to the present invention, a method for efficiently separating a nucleic acid from a specimen containing a nucleic acid, a device therefor, and a reagent therefor are provided.

DESCRIPTION OF EMBODIMENTS

<Method for Separating Nucleic Acid>

Figure 1:
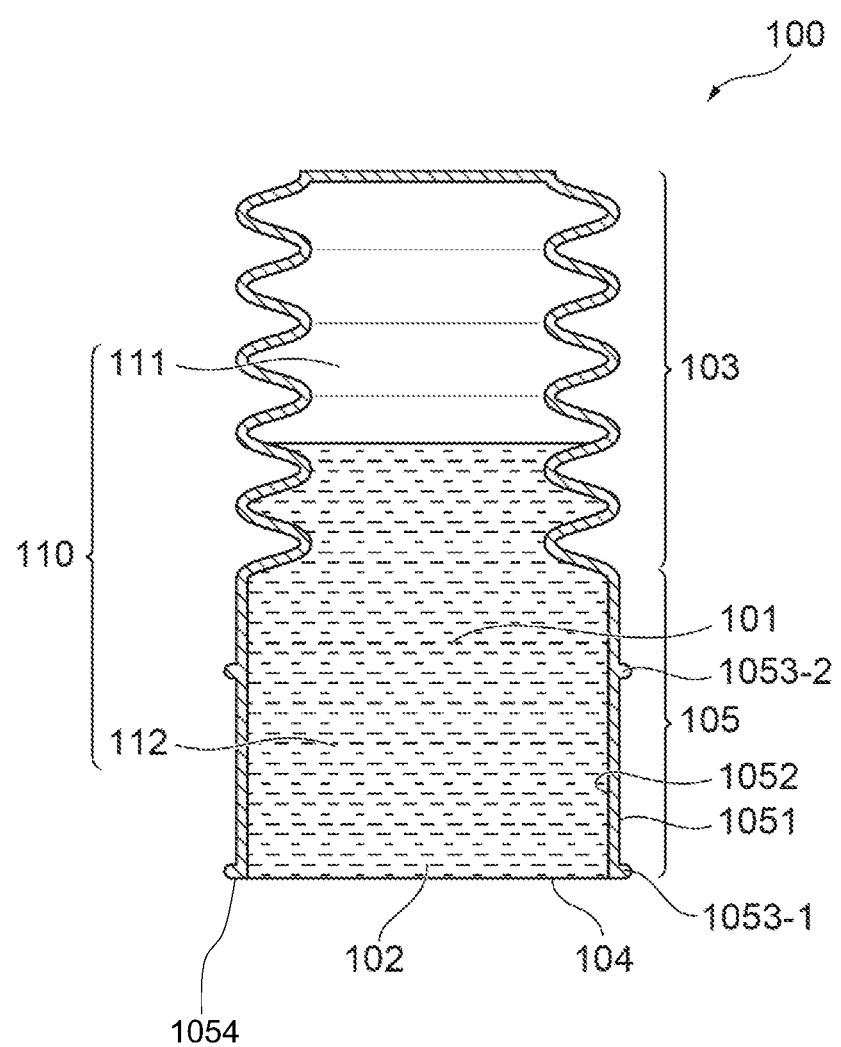
FIG. 1 schematically illustrates a cross-sectional view of a treatment reagent-accommodating container in one embodiment.

The present invention relates to a method for separating a nucleic acid from a specimen containing a nucleic acid using a treatment reagent-accommodating container and a nucleic acid-collecting member. One specific example of the treatment reagent-accommodating container is a treatment reagent-accommodating container 100 illustrated in FIG. 1. One specific example of the nucleic acid-collecting member is a nucleic acid-collecting member 200 illustrated in FIG. 2. The instruments used in the present invention and methods using the same are described below with reference to the embodiments illustrated in the drawings. However, the present invention is not limited to such embodiments.

A treatment reagent-accommodating container 100 accommodates a treatment reagent for causing a nucleic acid in a specimen to be released 101 in its inner container space 110 and has a discharge opening 102 for discharging the treatment reagent 101. Further, the treatment reagent-accommodating container 100 is configured such that the volume of the inner container space 110 can be reduced. One example of specific means for achieving such configuration is a pressure-feeding unit 103 described below. A cover 104 that seals the discharging opening 102 is attached to the discharge opening 102 such that the treatment reagent 101 is retained in the inner container space 110.

The discharging opening 102 of the treatment reagent-accommodating container 100 illustrated in FIG. 1 is formed as the circumference border thereof is surrounded by a discharging opening periphery portion 105. One end of the discharge opening periphery portion 105 is opened so as to surround the discharge opening 102, and the other end thereof is connected to the pressure-feeding unit 103. The discharge opening periphery portion 105 preferably has, but is not limited to, a tubular shape as illustrated in the figure. The inner container space 110 is a space formed by combining a pressure-feeding unit inner space 111 that is the inner space of the pressure-feeding unit 103 and a discharge opening adjacent space 112 that is the space surrounded by the discharging opening periphery portion 105. The pressure-feeding unit 103 is configured such that the volume of the pressure-feeding unit inner space 111 can be reduced. As the volume of the pressure-feeding unit inner space 111 decreases, the volume of the inner container space 110 also decreases accordingly.

By activating the pressure-feeding unit 103 to reduce the volume of the inner container space 110, it is possible to pressure-feed a mixture 421 described below out of the discharge opening 102. Note that "activating" the pressure-feeding unit 103 means operating the pressure-feeding unit 103 so as to reduce the volume of the inner container space 110, which means deforming the pressure-feeding unit 103 in the embodiment illustrated in figures.

The pressure-feeding unit 103 preferably has, but is not limited to, a tubular body having walls forming an accordion structure, which is extendable and contractible in its axial direction and has an end portion that is not connected to the discharging opening periphery portion 105 is closed or closable, as illustrated in FIG. 1. The illustrated pressure-feeding unit 103 having an accordion structure is an example of a partial structure of the treatment reagent-accommodating container 100 that is deformable such that the volume of the inner container space 110 can be reduced. However, the form of the pressure-feeding unit 103 is not limited to such tubular body having an accordion structure. The pressure-feeding unit 103 in any form can be used as long as it has an opening that is connected to the discharge opening periphery portion 105 and comprises the other portion that is a closed or closable bag which is deformable such that the volume of the inner container space 110 can be reduced. The pressure-feeding unit 103, which is deformable as described above, is configured such that it can preferably be elastically deformed, and it can more preferably make the inner container space 110 deformed to reduce the volume thereof and then restore the volume and shape of the inner container space 110 under conditions that cause no pressure difference inside and outside of the inner container space 110. Another example of the pressure-feeding unit 103 is a combination of a tubular body having one end that is connected to the discharge opening periphery portion 105 and a piston that is accommodated in the tubular body, the piston having a side wall that is in contact with the interior wall of the tubular body and is slidable along the axial direction of the tubular body while the inner wall of the tubular body and the side wall do not cause air leakage, which can reduce the volume of each of the pressure-feeding unit inner space 111 and the inner container space 110 formed inside the tubular body through movement of the piston.

Each of the illustrated discharge opening periphery portion 105 and the pressure-feeding unit 103 has a circular cross-section that is on a plane perpendicular to the direction in which the treatment reagent 101 is released. However, the shape of the cross-section is not limited and it may be a polygonal shape such as a quadrangle (square or rectangle), a triangle, or a pentagon. The circular shape includes an exact circle, an ellipse, a flattened shape of an exact circle, a deformed ellipse. The polygonal shape includes a shape having round corners.

The cover 104 that seals the discharge opening 102 of the treatment reagent-accommodating container 100 is configured to be broken when the treatment reagent-accommodating container 100 is connected to the treatment reagent-supplying opening of the nucleic acid-collecting member 200 as described in detail separately. The cover 104 may be formed with a film comprising a synthetic resin, a metal film such as an aluminum film, or a laminated body of different kinds of films. The cover 104 can be fixed to the end portion surrounding the discharge opening 102 of the discharging opening periphery portion 105 by means of adhesion with an adhesive, thermal or ultrasonic welding, or the like.

It is preferable to form one or more ring-shaped protrusions 1053-1, 1053-2, which extends in a circumferential direction so as to surround the whole circumference of the discharging opening periphery portion 105 and protrudes outwardly in a radial direction, on the external circumference surface 1051 of the discharge opening periphery portion 105 of the treatment reagent-accommodating container 100. The functions of the ring-shaped protrusions 1053-1, 1053-2 are described below. Preferably, at least the ring-shaped protrusions 1053-1, 1053-2 are formed with a compressible and deformable material in the treatment reagent-accommodating container 100.

The composition of the treatment reagent for causing a nucleic acid in a specimen to be released 101 is separately described in detail.

Figure 2:
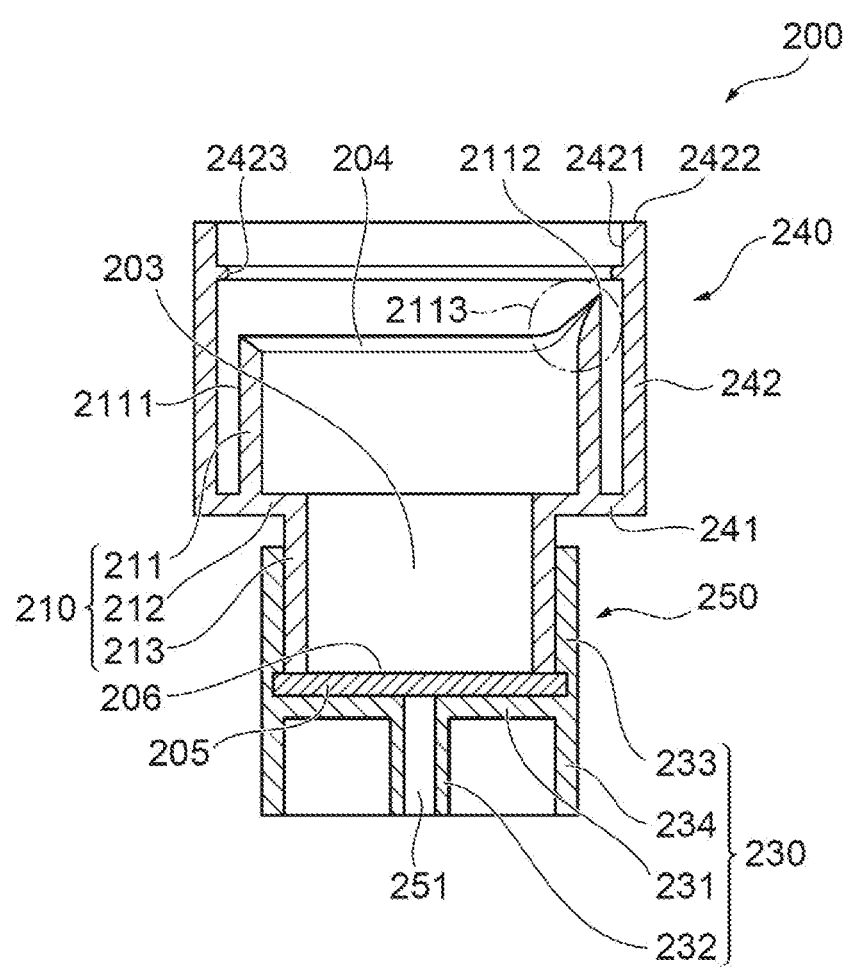
FIG. 2 schematically illustrates a cross-sectional view of a nucleic acid-collecting member in one embodiment.

The nucleic acid-collecting member 200 illustrated in FIG. 2 is configured to have an accommodation space 203 for accommodating a specimen, in which a treatment reagent-supplying opening 204 is formed on one side of the accommodation space 203 so as to be connected to the treatment reagent-accommodating container 100, thereby allowing the treatment reagent 101 to be supplied, and a mixture-discharging opening 206 is formed on the other side of thereof so as to discharge a mixture 421 described below via a carrier 205 that adsorbs a nucleic acid released in the mixture 421 while allowing the mixture 421 to permeate therethrough, The nucleic acid-collecting member 200 comprises a circumference wall portion 210 that surrounds the circumference of an accommodation space 203. A part of the circumference wall portion 210 defining the circumference border of the treatment reagent-supplying opening 204 is designated as a treatment reagent-supplying opening periphery portion 211, and a part thereof defining the circumference of the mixture-discharging opening 206 is designated as a mixture-discharging opening periphery portion 213. In the illustrated embodiment, the portion connecting the treatment reagent-supplying opening periphery portion 211 and the mixture-discharging opening periphery portion 213 is designated as circumference wall-connecting portion 212. However, the circumference wall portion 210 is not limited to this embodiment and may be shaped into a tubular body in which the treatment reagent-supplying opening periphery portion 211 and the mixture-discharging opening periphery portion 213 have the same diameter in a continuous manner. The carrier 205 is disposed at the mixture-discharging opening 206 and configured such that when the mixture 421 formed in the accommodation space 203 is discharged from the mixture-discharging opening 206, the mixture permeates through the carrier 205. The carrier 205 is configured such that when the treatment reagent 101, the mixture 421, or a specimen S described below is accommodated in the accommodation space 203 in gravity under conditions that cause substantially no air pressure difference inside and outside the accommodation space 203 across the carrier 205, the treatment reagent 101, the mixture 421, or the specimen S is substantially unable to permeate through the carrier 205. Note that a state in which the treatment reagent 101, the mixture 421, or the specimen S is "substantially unable to permeate" through the carrier 205 refers to a state in which a minute amount of the treatment reagent 101, the mixture 421, or the specimen S is allowed to permeate therethrough unless it impairs the intended use of the present invention as well as a state in which no permeation is achieved. For example, the rate of permeation of the treatment reagent 101, the mixture 421, or the specimen S in gravity is less than 10 µL/second under the above conditions.

The circumference wall portion 210 and the carrier 205 may be connected to each other in an arbitrary manner. Preferably, the circumference wall portion 210 and the carrier 205 are connected in a separable manner. More preferably, as illustrated in FIG. 2, the nucleic acid-collecting member 200 comprises the specimen-receiving member 240 comprising the circumference wall portion 210 and a carrier-holding member 250 comprising the carrier 205 and a holding portion 230 holding the carrier 205, and the specimen-receiving member 240 and the carrier-holding member 250 are connected to each other in a separable manner.

Note that the holding portion 230 for holding the carrier 205 comprises: a main holding portion 231, which holds the carrier 205, and on which an opening is formed, the opening being the starting point of a discharge flow channel 251 which allows the mixture 421 that has permeated through the carrier 205 to pass therethrough; a flow channel periphery portion 232 which stands on the main holding portion 231 and defines the circumference of the discharge flow channel 251; a specimen-receiving member connecting portion 233 which stands on the circumference border of the main holding portion 231 on the side opposite to the side where there exists the flow channel periphery portion 232; and a discharged matter-accommodating container connecting portion 234 which stands on the circumference border of the main holding portion 231 on the side where there exists the flow channel periphery portion 232. The carrier 205 may be fixed to the holding portion 230. In the illustrated example, the carrier 205 is disposed on one face of the main holding portion 231 such that a part of the specimen-receiving member connecting portion 233 in the vicinity the holding portion 231 is positioned over the circumference border of the carrier 205, thereby holding and fixing the carrier 205. However, the holding portion 230 is not limited to this embodiment. In addition, the carrier 205 may be configured to be separable from the holding portion 230.

The specimen-receiving member connecting portion 233 of the carrier-holding member 250 and the mixture-discharging opening periphery portion 213 of the specimen-receiving member 240 may be configured such that one of them is fitted into (as illustrated) or screwed to (not illustrated) the other for the establishment of connection.

Figure 3:
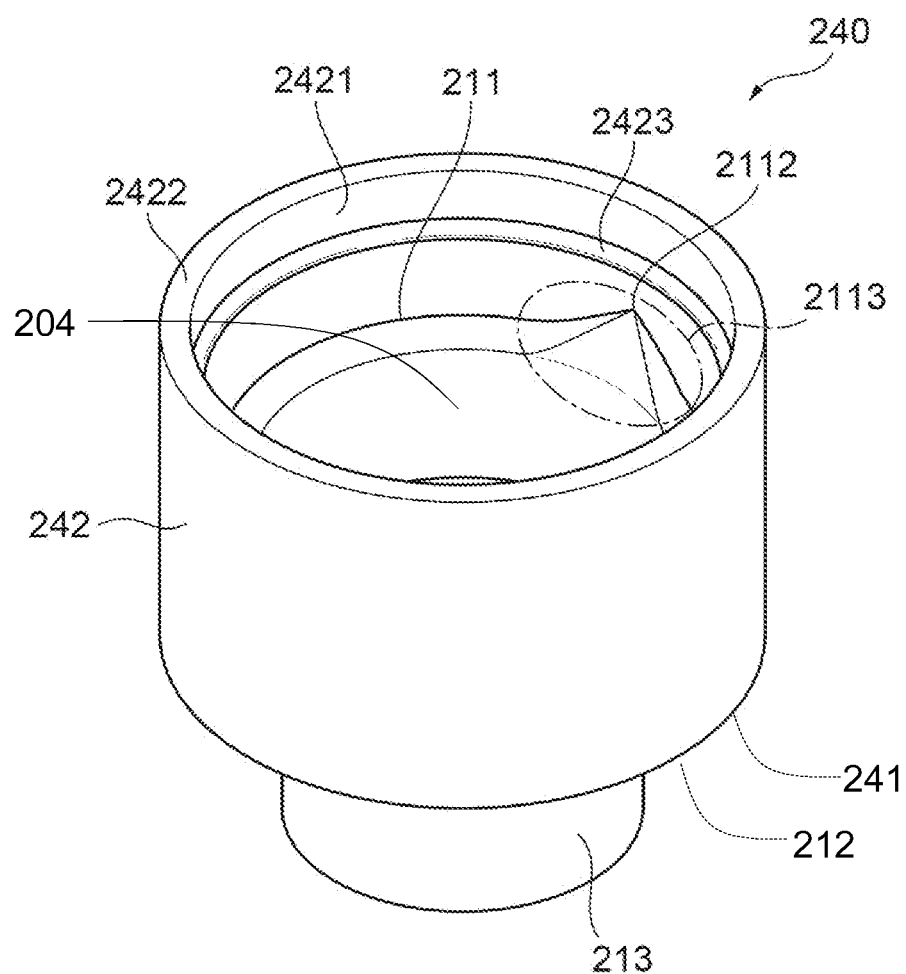
FIG. 3 schematically illustrates a cross-sectional view of a specimen-receiving member in one embodiment.

FIG. 3 illustrates a perspective view of a state in which the specimen-receiving member 240 comprising the circumference wall portion 210 illustrated in the cross-sectional view of FIG. 2 is separated from the carrier-holding member 250. The specimen-receiving member 240 in the illustrated embodiment further comprises: a flange portion 241 that protrudes outwardly from the external circumference surface of the circumference wall portion 210; and a mixture leakage-preventing wall portion 242 that stands from the circumference border of the flange portion 241 toward the side where there exists the treatment reagent-supplying opening 204 of the circumference wall portion 210, in addition to the circumference wall portion 210. An end portion 2422 of the mixture leakage-preventing wall portion 242 is formed such that it is disposed with a distance from the mixture-discharging opening 206, which is greater than a distance between the mixture-discharging opening 206 and an end portion 2112 on the side of the treatment reagent-supplying opening 204 of the treatment reagent-supplying opening periphery portion 211. This is preferable because the leakage preventing effect described below is further improved. Preferably, at least one ring-shaped wall surface protrusion 2423, which extends in a circumferential direction and protrudes inwardly in a radial direction, is formed on the internal circumference surface 2421 of the mixture leakage-preventing wall portion 242. The ring-shaped wall surface protrusion 2423 is preferably formed in the vicinity of the open-side end portion 2422 of the mixture leakage-preventing wall portion 242.

The nucleic acid-collecting member 200 consists of one member comprising a circumference wall portion 210 and a carrier 205 in another embodiment (not illustrated). For the nucleic acid-collecting member 200 in this embodiment, the circumference wall portion 210 may also have the structure illustrated in FIGS. 2 and 3. It is more preferable that the circumference wall portion 210 is combined with the flange portion 241 and the mixture leakage-preventing wall portion 242.

For the treatment reagent-supplying opening periphery portion 211 of the circumference wall portion 210 of the specimen-receiving member 240, an end portion 2112 surrounding the treatment reagent-supplying opening 204 is preferably a portion that is pressed against the cover 104 of the treatment reagent-accommodating container 100 so as to break the cover 104, thereby making an opening, when the treatment reagent-accommodating container 100 and the nucleic acid-collecting member 200 are connected to each other. Specifically, it is preferable for the end portion to have at least one sharp portion to break to the cover 104. In the illustrate example, the portion of the treatment reagent-supplying opening periphery portion 211, which surrounds the treatment reagent-supplying opening 204, is configured such that the wall thickness decreases, that is to say, the portion is sharpened, toward the open end portion. Further, it is preferable that the portion of the treatment reagent-supplying opening periphery portion 211, which surrounds the treatment reagent-supplying opening 204, comprises at least one protrusion 2113 that protrudes toward the side where the treatment reagent-accommodating container 100 is connected to the treatment reagent-supplying opening periphery portion 211. It is preferable that the protrusion 2113 is formed such that a cross-section formed on a plane perpendicular to the protruding direction is reduced, that is to say, the protrusion is sharpened, toward the end. In the illustrated example, only one protrusion 2113 is formed. However, a plurality of protrusions 2113 may be formed.

The discharge opening periphery portion 105 of the treatment reagent-accommodating container 100 and the treatment reagent-supplying opening periphery portion 211 of the circumference wall portion 210 of the nucleic acid-collecting member 200 may be configured such that one of them is fitted into (as illustrated) or screwed to (not illustrated) the other for the establishment of connection. The discharge opening periphery portion 105 and the treatment reagent-supplying opening periphery portion 211 usually have a tubular body shape such that they can fitted into or screwed to each other. More preferably, the treatment reagent-accommodating container 100 and the nucleic acid-collecting member 200 are configured to be connected to each other in a state in which an internal circumference surface 1052 of the discharging opening periphery portion 105 and an external peripheral surface 2111 of the treatment reagent-supplying opening periphery portion 211 are in contact with each other. Particularly, periphery portion 105 and the external circumference surface 2111 of the treatment reagent-supplying opening periphery portion 211 are configured such that they are in contact with each other to prevent the passage of the treatment reagent 101, the mixture 421, or the specimen S, and in particular, the passage of the mixture 421 therebetween, and the discharging opening periphery portion 105 and the treatment reagent-supplying opening periphery portion 211 can be fitted into or screwed to and preferably fitted into each other. At such time, the discharging opening periphery portion 105 and the treatment reagent-supplying opening periphery portion 211 may be fitted into or screwed to each other such that the internal circumference surface 1052 of the discharging opening periphery portion 105 and the external circumference surface 2111 of the treatment reagent-supplying opening periphery portion 211 are in contact with each other via a part of the broken cover 104.

In addition, the internal circumference surface 1052 of the discharging opening periphery portion 105 and the external circumference surface 2111 of the treatment reagent-supplying opening periphery portion 211 may be in contact with each other via a sealing material and are not necessarily in direct contact with each other as in the illustrated embodiment. The sealing material can comprise a compressible and deformable material such as rubber. It can be fixed to at least one of a portion of the internal circumference surface 1052 of the discharging opening periphery portion 105 and a portion of the external circumference surface 2111 of the treatment reagent-supplying opening periphery portion 211.

In an embodiment in which the nucleic acid-collecting member 200 has a mixture leakage-preventing wall portion 242, it is preferable that the treatment reagent-supplying opening periphery portion 211 of the circumference wall portion 210 and the mixture leakage-preventing wall portion 242 have respective tubular bodies which are disposed coaxially. In this embodiment, it is preferable that a distance between the external circumference surface 2111 of the treatment reagent-supplying opening periphery portion 211 and the internal circumference surface 2421 of the mixture leakage-preventing wall portion 242 is set to be slightly shorter than a distance between the apexes of the ring-shaped protrusions 1053-1, 1053-2 of the treatment reagent-accommodating container 100 and the internal circumference surface 1052 of a wall portion of the discharging opening periphery portion 105, and the ring-shaped protrusions 1053-1, 1053-2 are formed with a material that can be compressively deformed. The material preferably has elasticity. In this case, in step 2 described below, when the treatment reagent-accommodating container 100 and the nucleic acid-collecting member 200 are connected to each other, the external circumference surface 1051 of the discharging opening periphery portion 105 and the internal circumference surface 2421 of the mixture leakage-preventing wall portion 242 face each other, which causes the ring-shaped protrusion 1053-1, 1053-2 flanked between the external circumference surface 1051 of the discharging opening periphery portion 105 and the internal circumference surface 2421 of the mixture leakage-preventing wall portion 242 to be compressively deformed, thereby preventing the passage of the treatment reagent 101, the mixture 421, or the specimen S, and in particular, the passage of the mixture 421 between the external circumference surface 1051 of the discharging opening periphery portion 105 and the internal circumference surface 2421 of the mixture leakage-preventing wall portion 242. Further, in more preferable embodiment, when the treatment reagent-accommodating container 100 and the nucleic acid-collecting member 200 are connected to each other, the discharge opening periphery portion 105 is biased toward the treatment reagent-supplying opening periphery portion 211 across the ring-shaped protrusions 1053-1, 1053-2 that have been compressively deformed between the external circumference surface 1051 of the discharging opening periphery portion 105 and the internal circumference surface 2421 of the mixture leakage-preventing wall portion 242, thereby preventing the passage of the treatment reagent 101, the mixture 421, or the specimen S, and in particular, the passage of the mixture 421 between the external circumference surface 2111 of the treatment reagent-supplying opening periphery portion 211 and the internal circumference surface 1052 of the discharge opening periphery portion 105. In this embodiment, it is preferable that the discharging opening periphery portion 105 is formed with an elastically deformable material such that when the discharging opening periphery portion 105 is biased toward the treatment reagent-supplying opening periphery portion 211, the internal circumference surface 1052 of the discharging opening periphery portion 105 is biased toward the external circumference surface 2111 of the treatment reagent-supplying opening periphery portion 211.

In another embodiment that is not illustrated, a ring-shaped wall surface protrusion 2423 formed on the internal circumference surface 2421 of the mixture leakage-preventing wall portion 242 functions as with the ring-shaped protrusions 1053-1, 1053-2. Specifically, in such embodiment, a distance between the external circumference surface 1051 of the discharging opening periphery portion 105 and the internal circumference surface 2421 of the mixture leakage-preventing wall portion 242 is set to be slightly shorter than a distance between the apex of the ring-shaped wall surface protrusion 2423 and the internal circumference surface 2421 of the mixture leakage-preventing wall portion 242 (i.e., the height of the protrusion), and the ring-shaped wall surface protrusion 2423 is formed with a material that can be compressively deformed. The material preferably has elasticity. In this embodiment, unlike the illustrated embodiment, it is preferable that at least one ring-shaped wall surface protrusion 2423 is formed at a site where the external circumference surface 2111 of the treatment reagent-supplying opening periphery portion 211 and the internal circumference surface 2421 of the mixture leakage-preventing wall portion 242 face each other. Also in this embodiment, in step 2 described below, when the treatment reagent-accommodating container 100 and the nucleic acid-collecting member 200 are connected to each other, the ring-shaped wall surface protrusion 2423 flanked between the external circumference surface 1051 of the discharging opening periphery portion 105 and the internal circumference surface 2421 of the mixture leakage-preventing wall portion 242 is compressively deformed, thereby preventing the passage of the treatment reagent 101, the mixture 421, or the specimen S, and in particular, the passage of the mixture 421 between the external circumference surface 1051 of the discharging opening periphery portion 105 and the internal circumference surface 2421 of the mixture leakage-preventing wall portion 242. Further, the discharge opening periphery portion 105 is biased toward the treatment reagent-supplying opening periphery portion 211 across the ring-shaped wall surface protrusion 2423 that has been compressively deformed between the external circumference surface 1051 of the discharging opening periphery portion 105 and the internal circumference surface 2421 of the mixture leakage-preventing wall portion 242, thereby preventing the passage of the treatment reagent 101, the mixture 421, or the specimen S, and in particular, the passage of the mixture 421 between the external circumference surface 2111 of the treatment reagent-supplying opening periphery portion 211 and the internal circumference surface 1052 of the discharge opening periphery portion 105. Also in this case, it is preferable that the discharging opening periphery portion 105 is formed with an elastically deformable material.

The method for separating a nucleic acid of the present invention is described below with reference to FIGS. 4A to 4E.

A discharged matter-accommodating container 400 illustrated in the figures is prepared. A discharged matter-supplying opening 401 is formed on the discharged matter-accommodating container 400. A portion that defines the discharged matter-supplying opening 401 of the discharged matter-accommodating container 400 is designated as a discharged matter-supplying opening periphery portion 402.

Figure 4A:
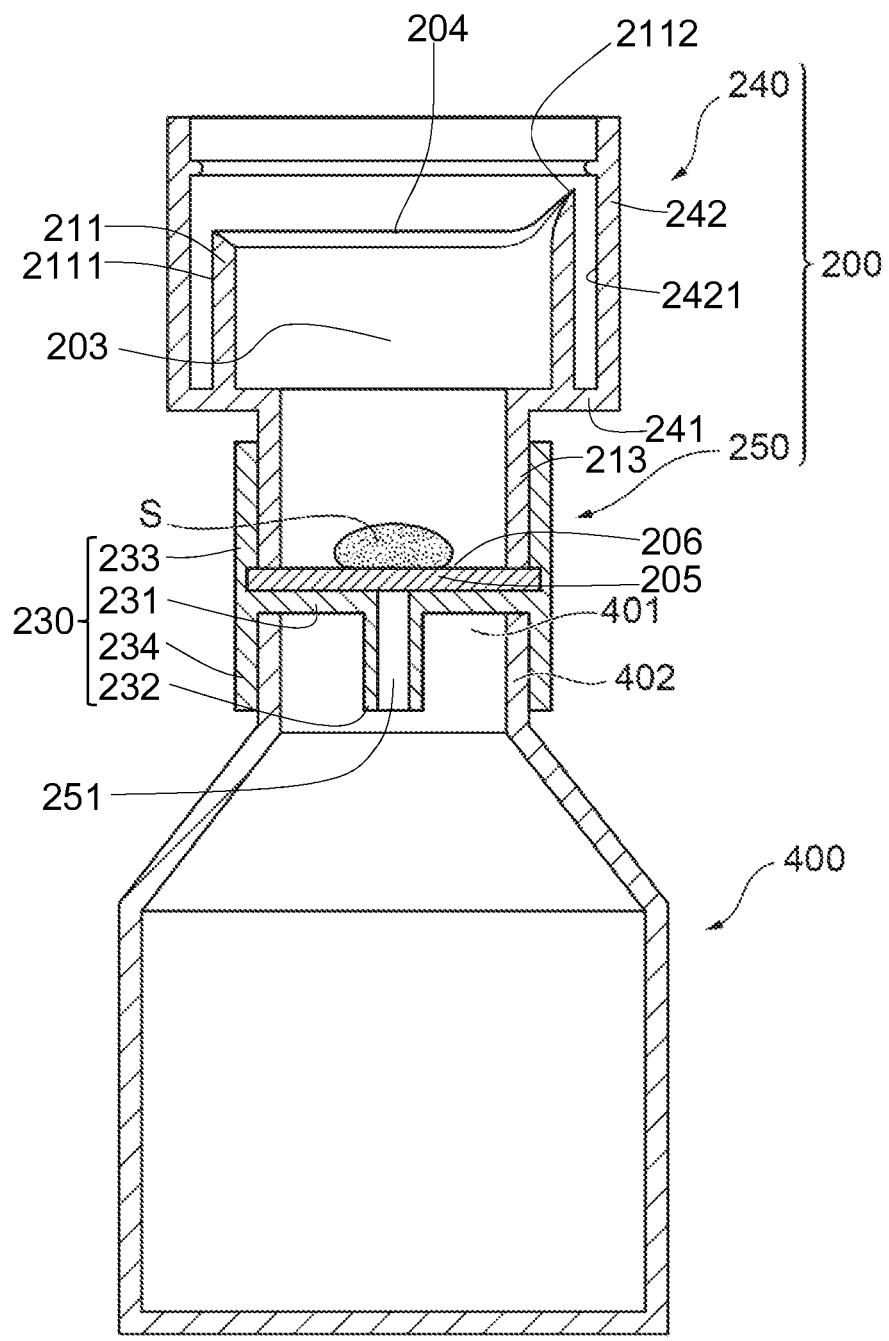
FIG. 4A is a schematic diagram explaining step 1 of the method for separating a nucleic acid of the present invention.

As illustrated in FIG. 4A, at first, a nucleic acid-collecting member 200 is combined with a discharged matter-accommodating container 400. In the illustrated embodiment, a discharged matter-accommodating container connecting portion 234 of the nucleic acid-collecting member 200 and a discharged matter-supplying opening periphery portion 402 of the discharged matter-accommodating container 400 are fitted into each other for establishing the connection therebetween. The discharged matter-accommodating container connecting portion 234 and the discharged matter-supplying opening periphery portion 402 may be configured such that they are fitted into each other for establishing the connection therebetween, which is not illustrated.

Next, step 1 of accommodating a specimen S that probably contains a nucleic acid in an accommodation space 203 of the collecting member 200 is carried out.

Figure 4B:
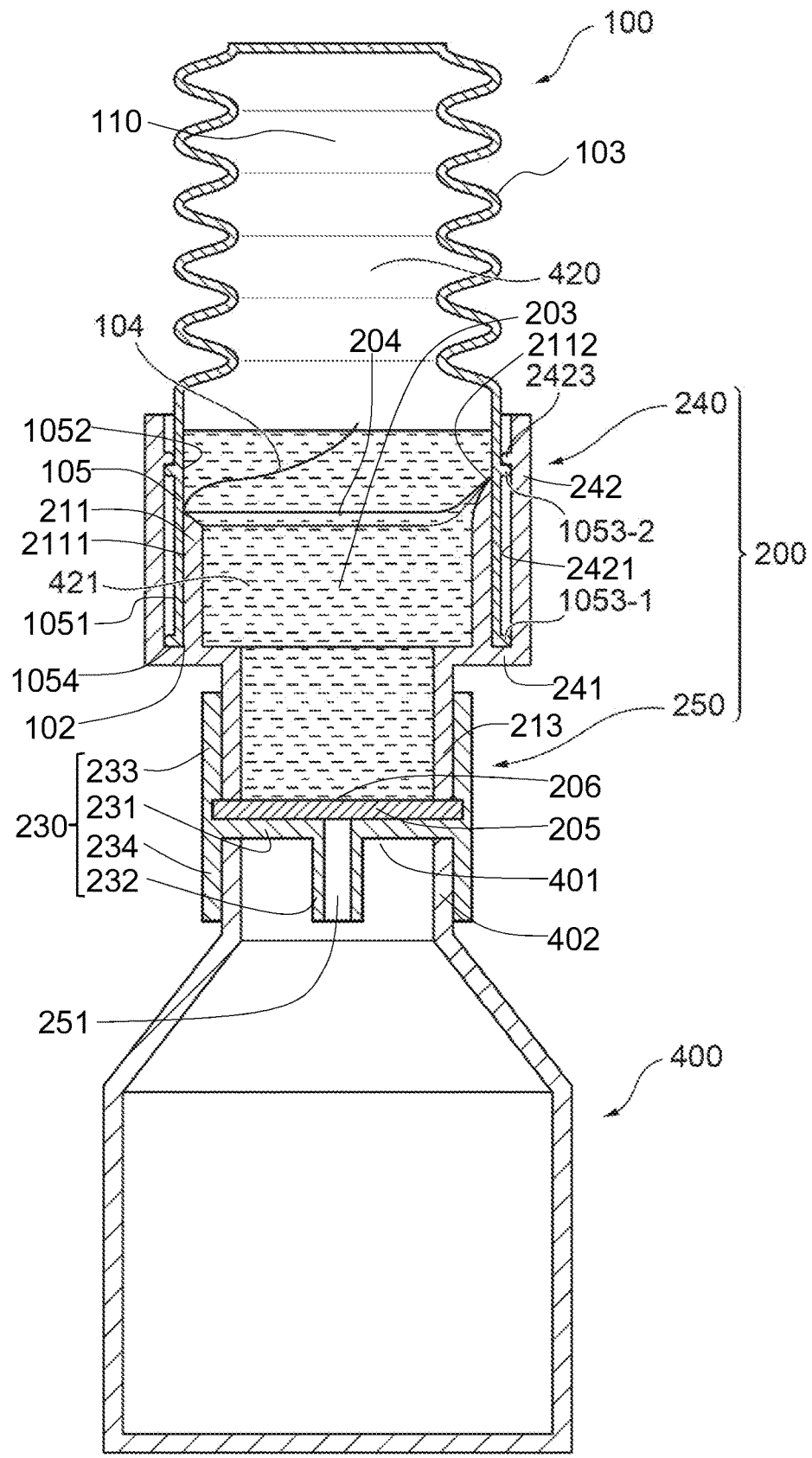
FIG. 4B is a schematic diagram explaining steps 2 and 3 of the method for separating a nucleic acid of the present invention.

As illustrated in FIG. 4B, step 2 of connecting the treatment reagent-accommodating container 100 to the treatment reagent-supplying opening 204 of the nucleic acid-collecting member 200, thereby causing the treatment reagent-supplying opening 204 to be communicated with the discharge opening 102 of the treatment reagent-accommodating container 100 is carried out following step 1. At such time, a cover 104 sealing the discharge opening 102 is broken by an end portion 2112 surrounding the treatment reagent-supplying opening 204 of the treatment reagent-supplying opening periphery portion 211, thereby making the discharging opening 102 opened. In the illustrate embodiment, both a discharge opening periphery portion 105 of the treatment reagent-accommodating container 100 and a treatment reagent-supplying opening periphery portion 211 of the nucleic acid-collecting member 200 have tubular bodies. They are configured such that the inner diameter of the discharging opening periphery portion 105 is approximately the same as the external diameter of the treatment reagent-supplying opening periphery portion 211 or the internal diameter of the discharging opening periphery portion 105 is slightly greater than the external diameter of the treatment reagent-supplying opening periphery portion 211. The treatment reagent-supplying opening periphery portion 211 is internally connected to the discharging opening periphery portion 105 so as to be fitted thereinto or screwed thereto.

In the illustrated embodiment, the nucleic acid-collecting member 200 further has a mixture leakage-preventing wall portion 242, and the treatment reagent-supplying opening periphery portion 211 of the circumference wall portion 210 and the mixture leakage-preventing wall portion 242 have respective tubular bodies which are disposed coaxially. In this embodiment, it is preferable that a distance between the external circumference surface 2111 of the treatment reagent-supplying opening periphery portion 211 and the internal circumference surface 2421 of the mixture leakage-preventing wall portion 242 is set to be shorter than a distance between the apexes of the ring-shaped protrusions 1053-1, 1053-2 of the treatment reagent-accommodating container 100 and the internal circumference surface 1052 of a wall portion of the discharging opening periphery portion 105, and the ring-shaped protrusions 1053-1, 1053-2 are formed with a material that can be compressively deformed. In such case, the discharge opening periphery portion 105 of the treatment reagent-accommodating container 100 is internally fitted into the mixture leakage-preventing wall portion 242 of the nucleic acid-collecting member 200, and the treatment reagent-supplying opening periphery portion 211 of the circumference wall portion 210 of the nucleic acid-collecting member 200 is internally fitted into the discharge opening periphery portion 105 of the treatment reagent-accommodating container 100. Then, an end portion 1054 of the discharge opening periphery portion 105 of the treatment reagent-accommodating container 100 and a flange portion 241 of the nucleic acid-collecting member 200 are brought into contact with each other by pressing. Accordingly, the cover 104 is broken by the end portion 2112 of the treatment reagent-supplying opening periphery portion 211. In addition, the surfaces of ring-shaped protrusions 1053-1, 1053-2 of the treatment reagent-accommodating container 100 and an internal circumference surface 2421 of the mixture leakage-preventing wall portion 242 are brought into contact throughout the whole circumference, thereby preventing leakage of a mixture 421. At the same time, the external circumference surface 2111 of the treatment reagent-supplying opening periphery portion 211 and an internal circumference surface 1052 of a wall portion of the discharging opening periphery portion 105 can be brought into contact with each other, thereby preventing the leakage of the mixture 421. With the above configuration, it is possible to reduce the risk that causes an operator to be in contact with the specimen S and the mixture 421 containing the specimen S. In this embodiment, the external circumference surface 2111 of the treatment reagent-supplying opening periphery portion 211 and the internal circumference surface 1052 of the wall portion of the discharging opening periphery portion 105 may be brought into contact with each other via a part of the broken cover 104.

In the illustrated embodiment, at least one pair of ring-shaped protrusions 1053-1, 1053-2 is formed on the external circumference surface 1051 of the discharge opening periphery portion 105 of the treatment reagent-accommodating container 100. In addition, at least one ring-shaped wall surface protrusion 2423 may be formed on the internal circumference surface 2421 of the mixture leakage-preventing wall portion 242. One of the ring-shaped protrusions 1053-1, 1053-2 (1053-2 in the illustrated example) and one of ring-shaped wall surface protrusions 2423 are engaged with each other such that the ring-shaped protrusion 1053-2 is positioned closer to the flange portion 241, compared to the ring-shaped wall surface protrusion 2423, thereby making it possible to prevent the treatment reagent-accommodating container 100 from being detached from the nucleic acid-collecting member 200. Specifically, the ring-shaped wall surface protrusion 2423 is formed on the mixture leakage-preventing wall portion 242. When the treatment reagent-accommodating container 100 and nucleic acid-collecting member 200 are connected to each other by pressing such that the end portion 1054 of the discharge opening periphery portion 105 of the treatment reagent-accommodating container 100 and the flange portion 241 of the nucleic acid-collecting member 200 are brought into contact with each other as described above. Accordingly, among the ring-shaped protrusions, the ring-shaped protrusion 1053-2 and the ring-shaped wall surface protrusion 2423 are engaged with each other such that the ring-shaped protrusion 1053-2 is positioned closer to the flange portion 241, compared to the ring-shaped wall surface protrusion 2423, thereby making it possible to prevent the treatment reagent-accommodating container 100 from being detached from the nucleic acid-collecting member 200. With the above configuration, it is possible to further reduce the risk that causes an operator to be in contact with the specimen S and the mixture 421 containing the specimen S.

In another embodiment that is not illustrated, the discharging opening periphery portion 105 is formed with an elastic material such that the external circumference surface 2111 of the treatment reagent-supplying opening periphery portion 211 and the internal circumference surface 1052 of the wall portion of the discharging opening periphery portion 105 are brought into contact with each other throughout the whole circumference, thereby preventing the leakage of the mixture 421. In this case, the external circumference surface 2111 of the treatment reagent-supplying opening periphery portion 211 and the internal circumference surface 1052 of the wall portion of the discharging opening periphery portion 105 may be brought into contact with each other via a part of the broken cover 104. In the above embodiment, it is possible to omit the ring-shaped protrusions 1053-1, 1053-2 of the treatment reagent-accommodating container 100.

In step 2, the mixing space 420 is formed by combining the inner container space 110 of the treatment reagent-accommodating container 100 and the accommodation space 203 of the nucleic acid-collecting member 200.

Subsequently, in step 3, a mixture is formed by mixing the specimen S and the treatment reagent 101 in the mixing space 420 formed in step 2 and a nucleic acid that may be contained in the specimen S is released in the mixture. The mixture of the specimen S and the treatment reagent 101 is designated as a mixture 421. As a result of the connection of the treatment reagent-accommodating container 100 and the nucleic acid-collecting member 200 in step 2, the air pressure inside the mixing space 420 becomes slightly higher than the air pressure inside the discharged matter-accommodating container 400 in some cases. However, a carrier 205 contained in the nucleic acid-collecting member 200 is configured such that the mixture 421 in the mixing space 420 is substantially unable to permeate in gravity through the carrier 205 under conditions that do not allow a pressure-feeding unit 103 to be activated, that is to say, under conditions that do not allow the volume of the inner container space 110 and the volume of the mixing space 420 to be reduced. More preferably, even in a case described below in which the mixture 421 is mixed by shaking in the mixing space 420 in step 3, the mixture 421 is substantially unable to permeate through the carrier 205. Note that a state in which the mixture 421 is "substantially unable to permeate" through the carrier 205 refers to a state in which a minute amount of the mixture 421 is allowed to permeate therethrough unless it impairs the intended use of the present invention as well as a state in which no permeation is achieved. For example, the rate of permeation of the mixture 421 is less than 10 µL/second. For sufficient elution of the nucleic acid, it is preferable to sufficiently mix the mixture 421 in the mixing space 420 by manually sufficiently and entirely shaking the treatment reagent-accommodating container 100, the nucleic acid-collecting member 200, and the discharged matter-accommodating container 400, which are connected to one another in the manner illustrated in FIG. 4B, thereby sufficiently stirring the mixture 421 in the mixing space 420. Step 3 can be carried out at room temperature (around 20° C. to 30° C.). It is preferable to allow the mixture to stand still for 3 to 7 minutes after mixing to facilitate the release of the nucleic acid.

Figure 4C:
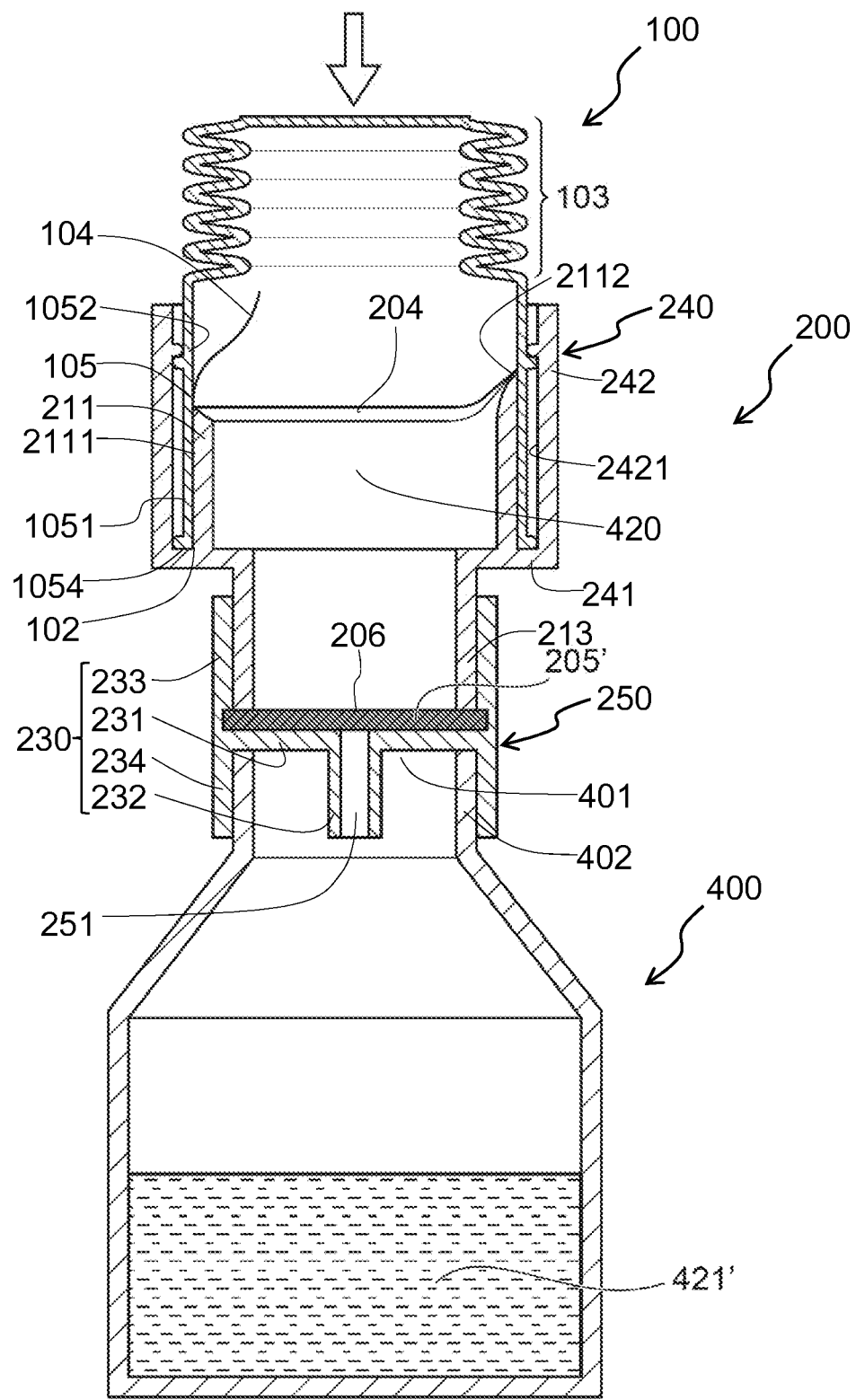
FIG. 4C is a schematic diagram explaining step 4 of the method for separating a nucleic acid of the present invention.

Subsequently, step 4 is carried out. Step 4 is a step of pressure-feeding the mixture 421 containing the nucleic acid released in step 3 by activating the pressure-feeding unit 103 of the treatment reagent-accommodating container 100, i.e., reducing the volume of the inner container space 100 and the volume of the mixing space 420, thereby discharging the mixture from a mixture-discharging opening 206 of the nucleic acid-collecting member 200 via the carrier 205 as illustrated in FIG. 4C. The discharged matter-accommodating container 400 and the nucleic acid-collecting member 200 are not connected in a complete air tight manner, and thus, the space inside the discharged matter-accommodating container 400 is in contact with the ambient air. When the air pressure inside the mixing space 420 is increased by activating the pressure-feeding unit 103 (compressing and deforming the pressure-feeding unit 103 having an accordion structure so as to reduce the volume of the inner container space 110 and the volume of the mixing space 420 in the illustrated example), the mixture 421 is allowed to permeate through the carrier 205 and pass through from the mixture-discharging opening 206 to the discharge flow channel 251 so as to be discharged into the discharged matter-accommodating container 400. At such time, the existing nucleic acid released and present in the mixture 421 is adsorbed by the carrier 205, and the other components of the mixture 421 are discharged into the discharged matter-accommodating container 400. In FIG. 4C, the carrier 205 after the completion of step 4 is particularly specified as a carrier 205' and the mixture 421 discharged after the completion of step 4 is particularly specified as a mixture 421'.

A step of collecting the nucleic acid adsorbed to the carrier 205' in step 4 is appropriately carried out. A method for collecting the nucleic acid is not particularly limited.

Figure 4D:
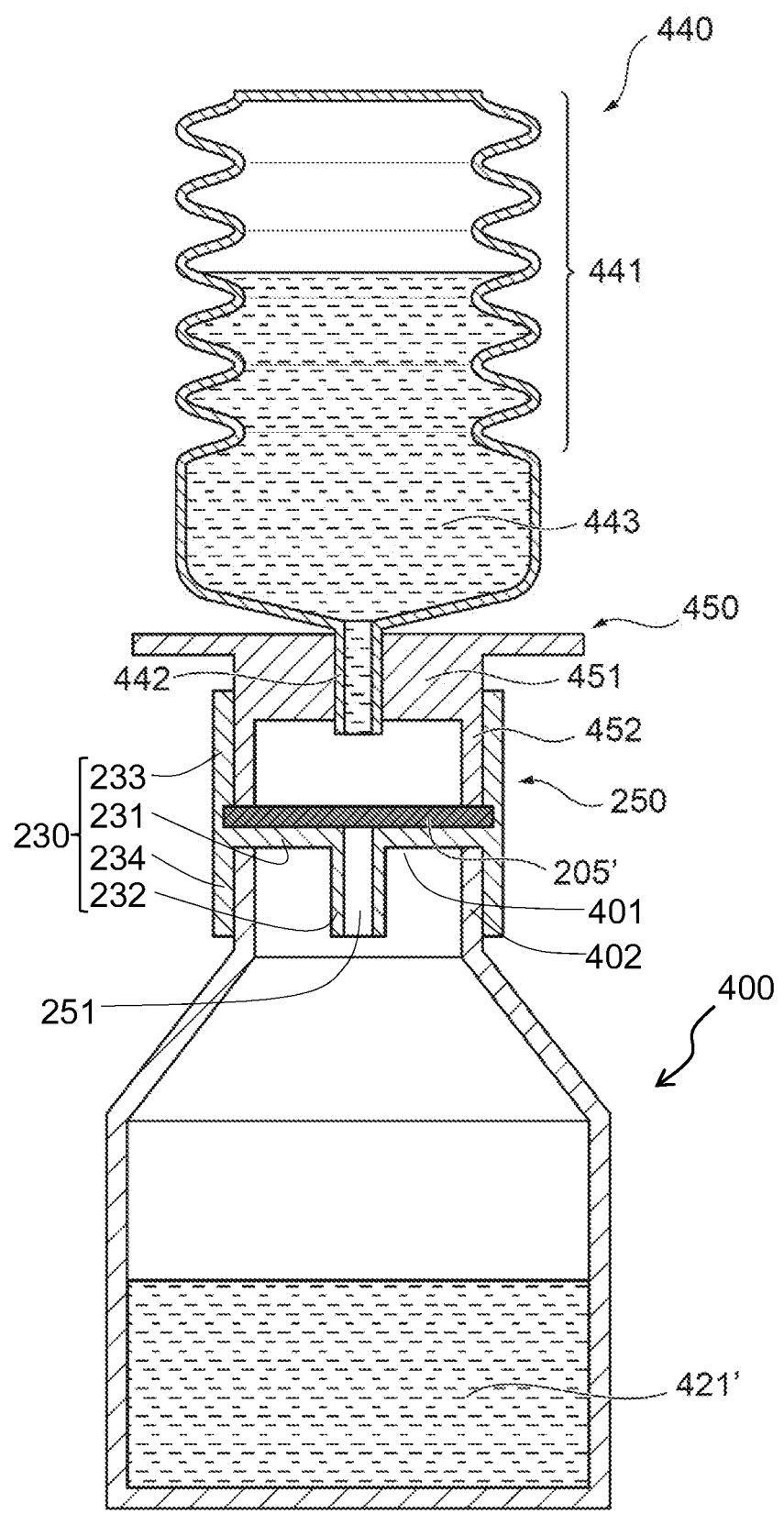
FIG. 4D is a schematic diagram explaining step 5 of the method for separating a nucleic acid of the present invention.

Typically, step 5 of washing the carrier 205' using a washing liquid, thereby removing unnecessary components other than a nucleic acid from the carrier, following step 4 is carried out. One example of the configuration of a device for carrying out step 5 is illustrated in FIG. 4D. The treatment reagent-accommodating container 100 and the specimen-receiving member 240 are removed from the device after the completion of step 4 illustrated in FIG. 4C, and the carrier-holding member 250 and the discharged matter-accommodating container 400 are left. Subsequently, as illustrated in FIG. 4D, the washing liquid-accommodating container 440 is connected to the carrier-holding member 250 via the connecting member 450, if appropriate. The washing liquid-accommodating container 440 is not particularly limited as long as it accommodates the washing liquid 443. However, it preferably includes a pressure-feeding unit 441 and a washing liquid-discharging neck portion 442 in which a discharge flow channel of a washing liquid 443 is formed. A specific embodiment and other embodiments of the pressure-feeding unit 441 are the same as described for the pressure-feeding unit 103 of the treatment reagent-accommodating container 100. The connecting member 450 comprises a connecting member body 451, on which a through-hole having a shape corresponding to a washing liquid-discharging neck portion 442 is formed, and a connecting member connecting portion 452. The washing liquid-discharging neck portion 442 and the through-hole of the connecting member body 451 may be configured such that one of them is fitted into or screwed to the other for the establishment of connection. The connecting member connecting portion 452 and the specimen-receiving member connecting portion 233 of the carrier-holding member 250 may be configured such that one of them is fitted into or screwed to the other for the establishment of connection. In step 5, as illustrate in FIG. 4D, in a state in which the washing liquid-accommodating container 440 is connected to the carrier-holding member 250 via the connecting member 450, the pressure-feeding unit 441 is activated to pressure-feeding the washing liquid 443 so as to allow the washing liquid to permeate through the carrier 205', thereby removing unnecessary components other than the nucleic acid. The discharged liquid is mixed with the mixture 421' in the washing liquid-accommodating container 440 in step 4 and is regarded as waste so as to be discarded. The carrier containing the nucleic acid, from which unnecessary components have been removed by washing in step 5, is particularly specified as carrier 205".

Figure 4E:
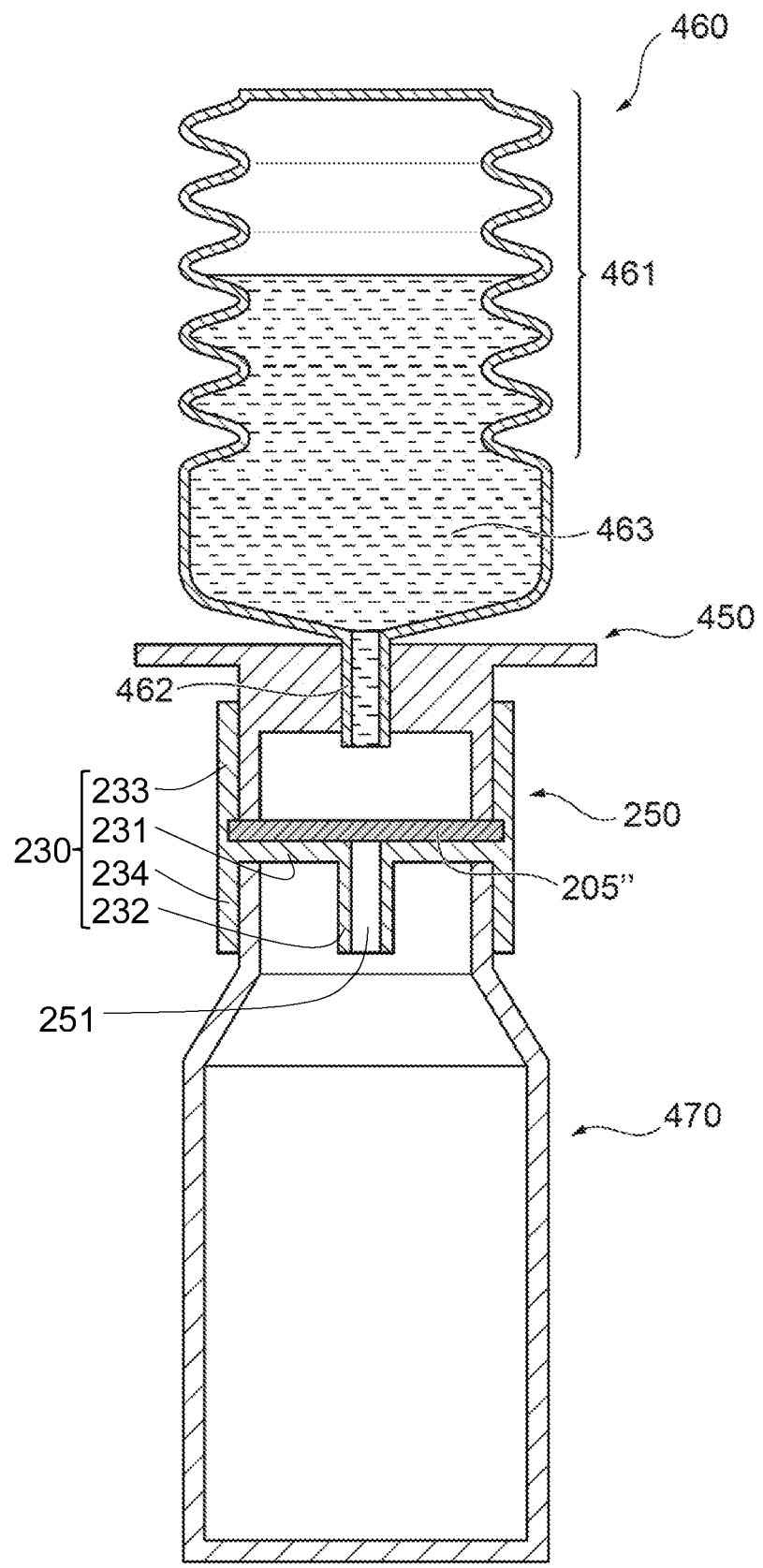
FIG. 4E is a schematic diagram explaining step 6 of the method for separating a nucleic acid of the present invention.

It is preferable to carry out step 6 of bringing an eluent for eluting a nucleic acid into contact with the carrier, thereby eluting the nucleic acid from the carrier, following step 5. One example of the configuration of a device for carrying out step 6 is illustrated in FIG. 4E. After step 5 is carried out using the device illustrated in FIG. 4D, the discharged matter-accommodating container 400 and the washing liquid-accommodating container 440 are removed and the carrier-holding member 250 containing the carrier 205" and the connecting member 450 are left. Subsequently, the nucleic acid-collecting container 470 is disposed downstream of the discharge flow channel 251 of the carrier-holding member 250. Then, the eluent-accommodating container 460 is installed to the connecting member 450. The eluent-accommodating container 460 used herein is not particularly limited as long as it accommodates an eluent 463. However, it preferably includes a pressure-feeding unit 461 and an eluent-discharging neck portion 462, in which a flow channel for discharging the eluent 463 is formed. A specific embodiment and other embodiments of the pressure-feeding unit 461 are the same as described for the pressure-feeding unit 103 of the treatment reagent-accommodating container 100. A through-hole formed on the connecting member body 451 of the connecting member 450 is configured to have a shape which also corresponds to the eluent-discharging neck portion 462. The eluent-discharging neck portion 462 and the through-hole of the connecting member body 451 may be configured such that one of them is fitted into or screwed to the other for the establishment of connection. In step 6, as illustrate in FIG. 4E, in a state in which the eluent-accommodating container 460 is connected to the carrier-holding member 250 via the connecting member 450, the pressure-feeding unit 461 is activated to pressure-feeding the eluent 463 so as to allow the washing liquid to permeate through the carrier 205", thereby eluting the nucleic acid adsorbed by the carrier 205". The discharge nucleic acid-containing liquid is accommodated in the nucleic acid-collecting container 470 and can be used as a nucleic acid extract from the specimen S for analysis.

It is preferable that the nucleic acid-containing liquid collected in step 6 contains a purified nucleic acid. Purification of a nucleic acid means separation and isolation of a nucleic acid contained in a specimen from foreign substances other than the nucleic acid. The degree of acceptable purification is at a level that allows implementation of the following examples of molecular biological analysis with the use of a purified nucleic acid without problems: nucleic acid amplification methods such as PCR and the isothermal nucleic acid amplification method, restriction enzyme treatment, cloning, nucleotide sequencing analysis, Southern blotting, Northern blotting, hybrid capture analysis, line probe assay, microarray analysis, electrophoresis, mass spectrometry, fluorescence staining, dye staining, and analysis based on complementary binding between natural or unnatural complementary nucleic acid strands.

<Device for Separating Nucleic Acid>

According to the present invention, a device for separating a nucleic acid from a specimen containing a nucleic acid is provided.

Preferably, the device of the present invention comprises the treatment reagent-accommodating container 100 and the nucleic acid-collecting member 200 described in detail relating to the aforementioned method. As the device of the present invention comprises a plurality of constituent elements, it can be also referred to as a "kit."

Preferably, the device of the present invention further comprises the washing liquid-accommodating container 440 and/or the eluent-accommodating container 460 described in detail relating to the aforementioned method.

The device of the present invention may optionally comprise at least one selected from the discharged matter-accommodating container 400, the connecting member 450, and the nucleic acid-collecting container 470 described in detail relating to the aforementioned method.

The device of the present invention or individual elements included in the device of the present invention may be incorporated into a part of any constituent element such as a nucleic acid preparation device, a nucleic acid amplification device, or a device for automatic analysis of nucleic acids.

<Treatment Reagent>

A treatment reagent for causing a nucleic acid in a specimen to be released contains a component for causing a nucleic acid to be released. Preferably, it further comprises at least one selected from a component for reducing infectivity of a microorganism and a component for facilitating a carrier to adsorb a nucleic acid. The treatment reagent may contain, as the above components or components other than the above components, a liquid medium such as water or an organic solvent.

Figure 5:
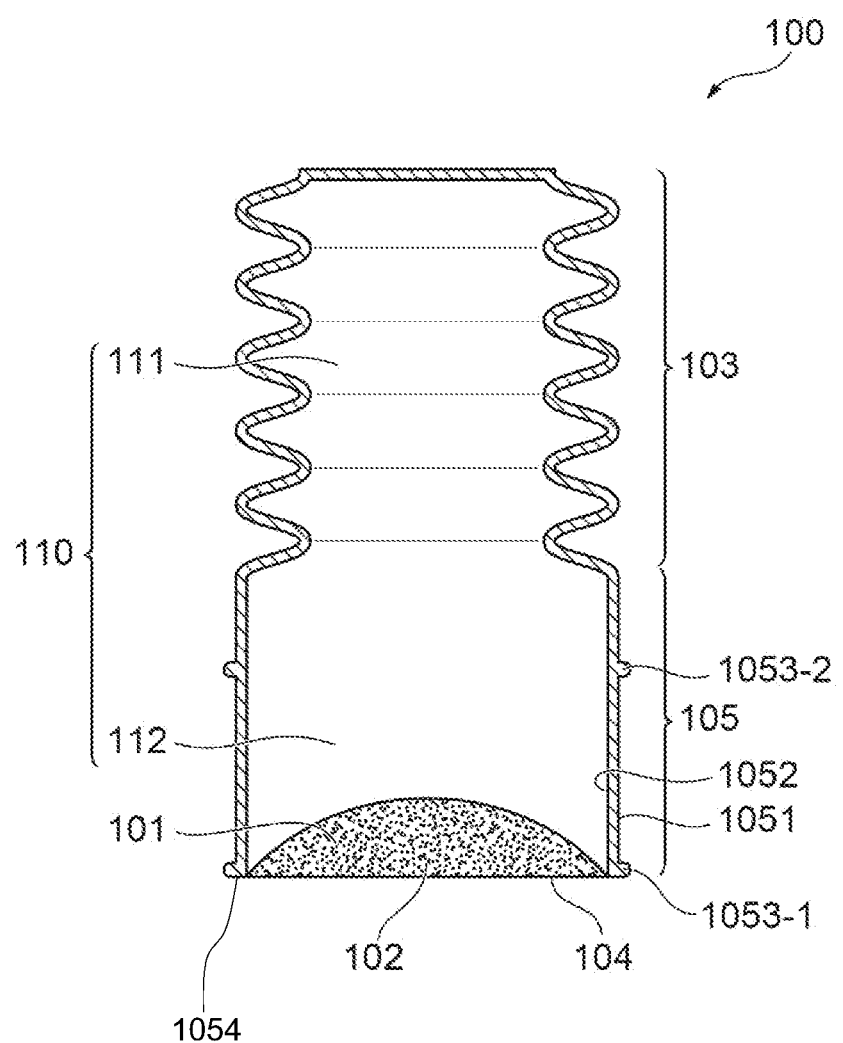
FIG. 5 schematically illustrates a cross-sectional view of the treatment reagent-accommodating container of the present invention in another embodiment.

The treatment reagent is in the liquid form in the embodiments illustrated in FIGS. 1 to 4D. However, it is not limited to the liquid form and thus it may be in the solid form. For example, in the embodiment of the treatment reagent-accommodating container 100 illustrated in FIG. 5, the treatment reagent 101 is in the solid form such as a powder or granule. Other features are similar to those of the treatment reagent-accommodating container 100 illustrated in FIG. 1.

It is preferable that at least one of the treatment reagent and the specimen contains a liquid such that a mixture formed by mixing the treatment reagent and the specimen is in the liquid form. For example, in a case in which the specimen contains a liquid such as urine, blood, beverage, river water, or sea water, the obtained mixture is in the liquid form even when the treatment reagent is in the solid form such as a powder or granule. In a case in which the specimen is in the solid form or solid-like form such as sputum or nasal discharge, the mixture can be obtained in the liquid form with the use of a liquid as the treatment reagent.

A component for reducing infectivity of a microorganism is a component capable of reducing infectivity of a microorganism that may be contained in a specimen. An agent that is generally used as a bactericide or a disinfectant can be used. Examples of a component for reducing infectivity of a microorganism include, but are not limited to, at least one component selected from the group consisting of an organic solvent, an aldehyde disinfectant, an iodine agent, a chlorine agent, peracetic acid, ozone, hydrogen peroxide, merbromin, 6,9-diamino-2-ethoxyacridine lactate, a surfactant, and an alkaline substance. Examples of a component for reducing infectivity of a microorganism component include, but are not limited to, at least one component (designated as a "first group component") selected from the group consisting of an organic solvent, glutaraldehyde, phtharal, peracetic acid, povidone iodine, sodium hypochlorite, benzalkonium chloride, and a surfactant. In addition, different examples of a component for reducing infectivity of a microorganism component include a component other than the first group component, which is at least one component selected from the group consisting of an organic solvent, an aldehyde disinfectant, an iodine agent, a chlorine agent, peracetic acid, ozone, hydrogen peroxide, merbromin, 6,9-diamino-2-ethoxyacridine lactate, a surfactant, and an alkaline substance. More specific examples include, but are not limited to, at least one component (designated as a "second group component") selected from the group consisting of ozone, hydrogen peroxide, chlorine dioxide, merbromin, chlorhexidine gluconate, 6,9-diamino-2-ethoxyacridine lactate, cetylpyridinium chloride, formaldehyde, and an alkaline substance. 6,9-Diamino-2-ethoxyacridine lactate in the form of monohydrate may be added.

Examples of an organic solvent include alcohols such as methanol, ethanol, and isopropanol and phenols such as phenol and cresol. An organic solvent may be a mixed solvent obtained by mixing different types of organic solvents. Examples of an aldehyde disinfectant include at least one selected from glutaraldehyde, phtharal, and formaldehyde. An example of an iodine agent is povidone iodine. Examples of a chlorine agent include at least one selected from hypochlorite and chlorine dioxide. An example of hypochlorite used herein is sodium hypochlorite. Examples of a surfactant include at least one selected from an anionic surfactant, a cationic surfactant, an amphoteric surfactant, and a nonionic surfactant. Examples of a cationic surfactant (invert soap) include at least one selected from benzalkonium chloride and cetylpyridinium chloride. An example of an amphoteric surfactant (amphoteric soap) is chlorhexidine gluconate. Examples of an alkaline substance include basic salts such as sodium carbonate as well as basic substances such as sodium hydroxide, potassium hydroxide, barium hydroxide, calcium hydroxide, tetramethylammonium hydroxide, ammonia, and trimethylamine, and more preferably include at least one selected from sodium hydroxide and potassium hydroxide. The amount of a component for reducing infectivity of a microorganism of the present invention may be an effective amount that allows reducing infectivity of a microorganism contained in a specimen. The concentration and amount of a component for reducing infectivity of a microorganism differ in the optimum point depending on components. However, those skilled in the art can readily determine the optimum point.

According to the present invention, the "release" of a nucleic acid means a state in which a nucleic acid to be separated, which is present in a specimen, can be adsorbed by a carrier. For example, in a case in which a nucleic acid is encapsulated with a biological membrane of a cell, virus, or the like in a specimen, the release means a state in which the biological membrane is destroyed to release the nucleic acid outside the biological membrane such that the nucleic acid can be adsorbed by the carrier.

As a component for causing a nucleic acid to be released, a component capable of solubilizing a membrane encapsulating a nucleic acid in a specimen (e.g., biological membrane of a cell or virus) can be used. Examples thereof include at least one selected from the group consisting of alkaline substances and surfactants. The amount of a component for causing a nucleic acid to be released used in the present invention may be an effective amount that allows causing a nucleic acid to be released in a specimen.

An alkaline substance serves as a component for causing a nucleic acid to be released as well as a component for reducing infectivity of a microorganism. An alkaline substance which is an effective component for causing a nucleic acid to be released can be selected from the above specific examples of an alkaline substance as a component for reducing infectivity of a microorganism.

Examples of a surfactant include at least one selected from an anionic surfactant, a cationic surfactant, an amphoteric surfactant, and a nonionic surfactant. A surfactant serves as a component for causing a nucleic acid to be released as well as a component for reducing infectivity of a microorganism. A surfactant which is an effective component for causing a nucleic acid to be released can be selected from the above specific examples of a surfactant as a component for reducing infectivity of a microorganism.

Examples of a component for facilitating a carrier to adsorb a nucleic acid include organic solvents and chaotropic agents.

Examples of an organic solvent that is an effective component for facilitating a carrier to adsorb a nucleic acid include alcohols such as methanol, ethanol, and isopropanol, phenol, and chloroform. An organic solvent may be a mixed solvent obtained by mixing different types of organic solvents. Examples of a chaotropic agent include at least one selected from the group consisting of a guanidine salt (e.g., at least one selected from guanidine isothiocyanate, guanidine thiocyanate, and guanidine hydrochloride), urea, sodium iodide, potassium iodide, sodium bromide, potassium bromide, calcium bromide, ammonium bromide, sodium perchlorate, sodium cyanate, potassium cyanate, sodium thiocyanate, sodium perchlorate, sodium trichloroacetate, and sodium trifluoroacetate. A chaotropic agent is more preferably one selected from a guanidine salt, urea, and sodium iodide and most preferably a guanidine salt. These chaotropic agents may be used alone or in combination. In addition, a chaotropic agent functions not only to promote adsorption of a nucleic acid by a nucleic acid adsorptive carrier but also to serve as a protein denaturant, thereby also acting on extraction of the nucleic acid. The amount of a component for facilitating a carrier to adsorb a nucleic acid may be an amount enough to facilitate a carrier to adsorb a nucleic acid. Those skilled in the art can readily determine the optimum amount. However, for example, in a case in which a component for facilitating a carrier to adsorb a nucleic acid is an organic solvent, the amount accounts for 20% by weight or more and preferably 40% by weight or more with respect to the total amount of the treatment reagent. In a case in which a component for facilitating a carrier to adsorb a nucleic acid is a chaotropic agent, the final concentration of the component in a mixture when mixed with a specimen is 0.1 M or more, more preferably 0.5 M or more, and further preferably 1 M or more.

In order for a treatment reagent used in the present invention to have three advantageous features of reducing infectivity of a pathogenic microorganism contained in a specimen, causing a nucleic acid present in a specimen to be released, and allowing a nucleic acid adsorptive carrier to adsorb a nucleic acid, it is preferable to use a plurality of the aforementioned components in combination. In addition, one substance has multiple functions in some cases. For example, an organic solvent such as an alcohol functions as a component for reducing infectivity of a microorganism component and also functions as a component for facilitating a carrier to adsorb a nucleic acid. A component having multiple functions may be mixed in a treatment reagent.

A treatment reagent used in the present invention preferably contains a component for reducing infectivity of a microorganism and a component for causing a nucleic acid to be released. Each of the components is described above. A component for reducing infectivity of a microorganism and a component for causing a nucleic acid to be released are not necessarily different substances. At least one substance that functions as the two components may be used. An alkaline substance and a surfactant are each a component that can reduce infectivity of a microorganism and also can cause a nucleic acid to be release as described above. Therefore, the treatment reagent used in the present invention may contain at least one selected from the group consisting of alkaline substances and surfactants serving as a component that can reduce infectivity of a microorganism and also can cause a nucleic acid to be release. More preferably, the treatment reagent further contains a component for reducing infectivity of a microorganism, in addition to the above at least one member. The amount of at least one selected from the group consisting of alkaline substances and surfactants in the treatment reagent used in the present invention may be an effective amount that allows reducing infectivity of a microorganism and causing a nucleic acid to be released. Specifically, the concentration of an alkaline substance is preferably 0.1% by weight or more, more preferably more than 2% by weight, further preferably 3% by weight or more, and yet further preferably 4% by weight or more with respect to the total amount of the treatment reagent. The upper limit thereof is not particularly limited. However, it is preferably 20% by weight or less and more preferably 10% by weight or less. The concentration of the surfactant is preferably 0.05% by weight or more and more preferably 0.1% by weight or more, and at the same time, it is preferably 5% by weight or less and more preferably 2% by weight or less with respect to the total amount of the treatment reagent.

Figure 6:
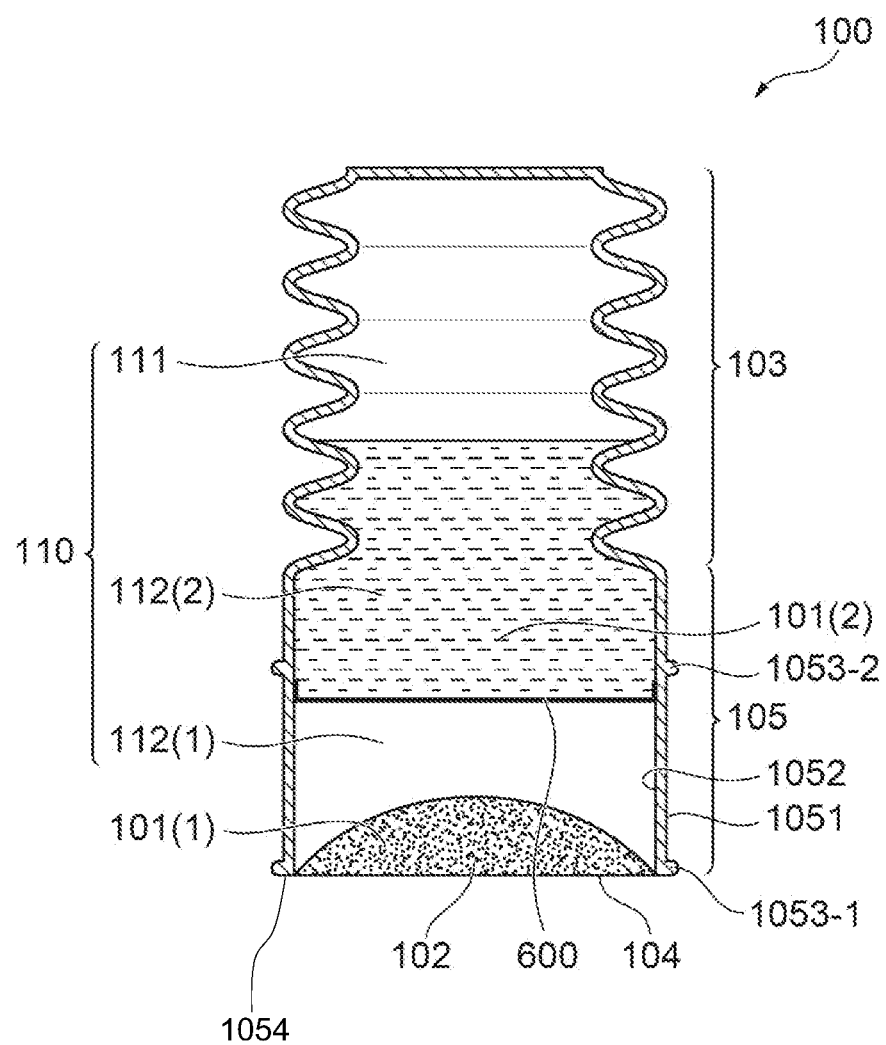
FIG. 6 schematically illustrates a cross-sectional view of the treatment reagent-accommodating container of the present invention in yet another embodiment.

The treatment reagent used in the present invention is not necessarily accommodated, as a single component, in the inner container space 110 of the treatment reagent-accommodating container 100. It may be accommodated as separate components. In such case, the inner container space 110 is divided into a plurality of compartments, and each compartment can accommodate at least one treatment reagent. For example, in one embodiment of the treatment reagent-accommodating container 100 illustrated in FIG. 6, a partition 600 is provided between one end of the discharging opening periphery portion 105 on the side of the discharging opening 102 and the other end thereof which is connected to the pressure-feeding unit 103. The partition 600 is to separate the discharging opening adjacent space 112 into a discharging opening adjacent space discharging opening side portion 112 (1) and a discharging opening adjacent space pressure-feeding unit side portion 112 (2), thereby dividing the inner container space 110 into a discharging opening adjacent space discharging opening side portion 112 (1) and a space formed by combining the pressure-feeding unit inner space 111 and the discharge opening adjacent space pressure-feeding unit side portion 112 (2). In this embodiment, the treatment reagent contains a first treatment reagent 101 (1) and a second treatment reagent 101 (2). The first treatment reagent 101 (1) is accommodated in the discharging opening adjacent space discharging opening side portion 112 (1), and the second treatment reagent 101 (2) is accommodated in a space formed by combining the pressure-feeding unit inner space 111 and the discharge opening adjacent space pressure-feeding unit side portion 112 (2). In the embodiment illustrated in FIG. 6, the first treatment reagent 101 (1) is a solid such as a powder or granule, and the second treatment reagent 101 (2) is a liquid. However, the treatment reagents are not limited to such embodiment. For example, both of the first treatment reagent 101 (1) and the second treatment reagent 101 (2) may be in the solid form or liquid form. In addition, the treatment reagent may be formed with three or more components. In this case, each component can be optionally determined to be in the form of liquid, solid, etc. The partition 600 that separates the inner container space 110 is configured such that when the treatment reagent-accommodating container 100 is connected to the treatment reagent-supplying opening 204 of the nucleic acid-collecting member 200, the partition 600 is destroyed as in the case of the cover 104. The partition 600 may be formed with a film comprising a synthetic resin and a metallic film such as an aluminum film, and it also may be a laminated body prepared by laminating different types of films, as in the case of the cover 104. The partition 600 can be fixed by appropriate fixation to the internal circumference surface 1052 of the discharging opening periphery portion 105 by means of adhesion with an adhesive, thermal or ultrasonic welding, or the like.

A preferable combination of components of the treatment reagent used in the present invention is a combination of an alcohol and an alkaline substance. In order to enhance the aforementioned three advantageous features, at least one component selected from the group consisting of chaotropic agents, surfactants, and disinfectants or the reductant described above may be added. A liquid medium such as water may be further contained. An alcohol is preferably at least one selected from the group consisting of methanol, ethanol, and isopropanol. An alkaline substance is preferably at least one selected from the group consisting of sodium hydroxide, a potassium hydroxide, a barium hydroxide, and calcium hydroxide, and more preferably at least one selected from sodium hydroxide and potassium hydroxide. A combination of ethanol and sodium hydroxide is more preferable. In a case in which the treatment reagent used in the present invention contains an alcohol and an alkaline substance, those skilled in the art can appropriately determine the concentrations thereof. In one example, the concentration of an alcohol is preferably 20% by weight or more and more preferably 40% by weight or more with respect to the total amount of the treatment reagent. The upper limit thereof is not particularly limited. However, it is preferably 99% by weight or less and more preferably 80% by weight or less. These alcohol concentrations are particularly preferable in a case in which the treatment reagent is in the liquid form. The concentration of an alkaline substance is preferably 0.1% by weight or more and more preferably 2% by weight or more with respect to the total amount of the treatment reagent. The upper limit thereof is not particularly limited. However, it is preferably 20% by weight or less and more preferably 10% by weight or less. These alkaline substance concentrations are particularly preferable in a case in which the treatment reagent is in the liquid form.

In a case in which the treatment reagent used in the present invention contains a chaotropic agent, the amount of a chaotropic agent corresponds to a final concentration of 0.1 M or more and more preferably 0.5 M or more when mixed with a specimen. The upper limit of the final concentration of a chaotropic agent is not particularly limited. However, it is preferably 10 M or less and more preferably 5 M or less.

In a case in which the specimen is a highly viscous specimen containing a component crosslinked by an S—S bond, such as sputum, it is preferable to mix a reductant, which is preferably a thiol reductant and particularly preferably a cysteine reductant such as N-acetyl-L-cysteine, L-cysteine, L-cysteine ethyl ester, L-cysteine methyl ester, N-ethyl-L-cysteine, or N-methyl-L-cysteine in a treatment reagent, thereby cleaving the S—S bond in the specimen to improve fluidity. As stated above, these reductants may be in the form of salts. The concentration of a reductant in the treatment reagent is preferably 0.5% by weight or more and more preferably 2% by weight or more. The upper limit thereof is not particularly limited. However, it is preferably 15% by weight or less and more preferably 10% by weight or less. These reductant concentrations are particularly preferable in a case in which the treatment reagent is in the liquid form.

<Nucleic Acid>

Examples of a nucleic acid in the present invention include deoxyribonucleotides and ribonucleotide polymers such as DNA and RNA. The origin of a nucleic acid is not particularly limited. A nucleic acid from a eukaryotic organism, a bacterium, an archaeon, a virus, a viroid, or an artificial composite may be used.

<Specimen Containing Nucleic Acid>

A specimen that can be used in the present invention is not particularly limited as long as it is a specimen containing a nucleic acid (including a specimen that possibly contains a nucleic acid). Examples of a specimen containing a nucleic acid include a biological sample, beverage, river water, and sea water. A biological sample may be obtained from an animal such as a human, a plant, or a microorganism. Examples of a biological sample include blood, urine, feces, sputum, saliva, nasal discharge, and swabbed fluid.

The present invention can be particularly preferably used for a specimen containing an infectious microorganism (including a specimen that possibly contains an infectious microorganism). An infectious microorganism can be a cause of infection. Examples of such specimen include a biological sample obtained from an animal or plant that is affected or possibly affected with infection and a food or beverage, river water, or sea water that is contaminated or possibly contaminated with an infectious microorganism.

According to the present invention, a nucleic acid in a specimen, which is to be separated, is not limited to a nucleic acid obtained from an infectious microorganism in a specimen, and it may be a nucleic acid obtained from different cells in a specimen, such as human cells or cells of another animal.

<Infectious Microorganism>

An infectious microorganism according to the present invention is a microorganism characterized by or capable of infecting a different organism and causing an infection in the host. Examples thereof include spirochaete such as syphilis (*Treponema* or *Borrelia*), pathogenic bacteria such as *staphylococcus*, *streptococcus*, *pneumococcus*, acid-fast bacterium (e.g., tuberculosis bacterium), tetanus *bacillus*, and *E. coli*, and pathogenic fungi. Examples of an infectious microorganism further include viruses such as influenza virus, adenovirus, herpesvirus, hepatitis virus, HIV virus, Japanese encephalitis virus, and poliovirus. In other words, the scope of the term "microorganism" used herein also includes viruses.

<Carrier that Adsorbs Nucleic Acid>

The term "carrier that adsorbs a nucleic acid" (hereinafter sometimes referred to as "nucleic acid adsorptive carrier") used in the present invention refers to a nucleic acid adsorptive carrier that can adsorb a released nucleic acid in the presence of a mixture of a treatment reagent and a specimen.

Examples of a carrier include, but are not limited to, an inorganic nucleic acid adsorptive carrier such as silica, a resin, and an organic nucleic acid adsorptive carrier such as an insoluble polysaccharide. Such nucleic acid adsorptive carriers may be in the form of powder, fibers, or porous material, and they may be magnetic and optionally modified. A nucleic acid adsorptive carrier that is formed to have a column shape, a membrane-like shape, or the like can be used. The thickness of a membrane-like nucleic acid adsorptive carrier is not particularly limited. However, it is preferably 1.0 mm to 1.5 mm. The plane view shape of a membrane-like nucleic acid adsorptive carrier is not particularly limited. However, it is preferably a circular shape having a diameter of 1 mm to 10 mm. One example of a porous nucleic acid adsorptive carrier is a porous carrier having a monolith structure, and monolith silica is particularly preferable. A particularly preferable example of monolith silica is monolith silica for which the mean value of through-pore diameters calculated based on a scanning electron microscope (SEM) image is preferably 5 to 50 μm and more preferably 5 to 40 μm.

As described in detail about the carrier 205, under conditions that cause substantially no air pressure difference between two spaces separated by a nucleic acid adsorptive carrier, the nucleic acid adsorptive carrier is preferably configured such that a treatment reagent 101, a mixture 421, or a specimen S disposed in one of the two spaces of the nucleic acid adsorptive carrier is substantially unable to permeate therethrough in gravity. The meaning of the expression "substantially unable to permeate" is described above relating to the carrier 205.

<Washing Liquid>

The washing liquid used in the present invention may be a washing liquid that can wash a solubilized reagent remaining in a nucleic acid adsorptive carrier adsorbing a nucleic acid or foreign substances from a sample. Examples thereof include, but are not limited to, an organic solvent, a water-soluble polymer solution, and a sugar aqueous solution, in which a nucleic acid is not dissolved.

Examples of an organic solvent that can be used as a washing liquid include ethanol, isopropanol, and acetone. In a case in which a water-soluble organic solvent is used as an organic solvent, an aqueous solution of an organic solvent can be used. Those skilled in the art can readily determine the optimum value of the concentration. However, for example, it is 20% to 100% by weight, preferably 30% to 90% by weight, and more preferably 40% to 80% by weight.

<Eluent>

An eluent used in the present invention is not particularly limited as long as it is a liquid that can elute a nucleic acid adsorbed by a nucleic acid adsorptive carrier. Examples of an eluent include water and buffer solutions such as a tris hydrochloride buffer solution. An eluent may contain components such as pH buffering components and salts as long as they do not inhibit the function of the eluent and PCR reaction.

<Materials that Constitute Components of the Device of the Present Invention>

As materials that constitute individual elements of the device of the present invention, materials that can be generally used for containers for preserving liquid can be used. Examples thereof include, but are not particularly limited to, synthetic resins such as polyethylene, polypropylene, polystyrene, polyethylene terephthalate, polyvinyl chloride, Teflon (registered trademark), acrylonitrile-butadiene-styrene, and acrylic. In addition, materials that can be generally used for containers for preserving liquid, such as glass or metal, may be used. It is also possible to use two or more of these examples in combination. In view of economic efficiency, a synthetic resin is preferable.

<Preferable Embodiment of the Treatment Reagent of the Present Invention>

A preferable embodiment of a treatment reagent for causing a nucleic acid to be released in a specimen containing a component crosslinked by an S—S bond, such as sputum, is a treatment reagent which further comprises a thiol reductant, in addition to the component for reducing infectivity of a microorganism and the component for causing a nucleic acid to be released. The treatment reagent in this embodiment can be particularly preferably used for causing a nucleic acid in a specimen containing a component crosslinked by an S—S bond, such as sputum, to be released and allowing a carrier comprising silica to adsorb the nucleic acid. At least one selected from N-acetyl-L-cysteine, L-cysteine, L-cysteine ethyl ester, L-cysteine methyl ester, N-ethyl-L-cysteine, N-methyl-L-cysteine, and salts of these compounds is preferable, and at least one selected from N-acetyl-L-cysteine, L-cysteine, L-cysteine ethyl ester, L-cysteine methyl ester and salts of these compounds is more preferable, and N-acetyl-L-cysteine is further more preferable as a thiol reductant. The concentration of a thiol reductant in the treatment reagent in this embodiment is described above. The treatment reagent is preferably an aqueous solution prepared by dissolving the component for reducing infectivity of a microorganism, the component for causing a nucleic acid to be released, and a thiol reductant in water. As the component for reducing infectivity of a microorganism and the component for causing a nucleic acid to be released, a component that can reduce infectivity of a microorganism and also can cause a nucleic acid to be released may be used. More preferably, a treatment reagent is an aqueous solution containing a thiol reductant in an amount that accounts for 0.5% by weight or more with respect to the total amount of the treatment reagent. The further preferable concentration is described above. The treatment reagent in this embodiment may further contain another component described above. Another component is preferably a chaotropic agent. The amount of a chaotropic agent is preferably an amount such that the final concentration of the chaotropic agent when mixed with a specimen is within the above scope.

The treatment reagent in this embodiment more preferably contains an alkaline substance and a thiol reductant and particularly preferably further contains an alcohol. The treatment reagent in this embodiment can be particularly preferably used for causing a nucleic acid in a specimen containing a component crosslinked by an S—S bond, such as sputum, to be released and allowing a carrier comprising silica to adsorb the nucleic acid. Specific examples of individual components are described above. In particular, at least one selected from sodium hydroxide and potassium hydroxide is preferable, and sodium hydroxide is more preferable as an alkaline substance, at least one selected from N-acetyl-L-cysteine, L-cysteine, L-cysteine ethyl ester, L-cysteine methyl ester, N-ethyl-L-cysteine, N-methyl-L-cysteine, and salts of these compounds is preferable, at least one selected from N-acetyl-L-cysteine, L-cysteine, L-cysteine ethyl ester, L-cysteine methyl ester and salts of these compounds is more preferable, and N-acetyl-L-cysteine is further more preferable as a thiol reductant, and ethanol is preferable as an alcohol. The concentration of a thiol reductant in the treatment reagent in this embodiment is described above. The concentration of an alkaline substance in the treatment reagent in this embodiment is preferably 0.1% by weight or more, more preferably more than 2% by weight, further preferably 3% by weight or more, and yet further preferably 4% by weight or more with respect to the total amount of the treatment reagent. The upper limit is not particularly limited. However, the concentration of an alkaline substance is preferably 20% by weight or less and more preferably 10% by weight or less. These alkaline substance concentrations are particularly preferable in a case in which the treatment reagent is in the liquid form. In a case in which the treatment reagent in this embodiment further contains alcohol, the concentration of alcohol is preferably 20% by weight or more, and more preferably 40% by weight or more with respect to the total amount of the treatment reagent. The upper limit thereof is not particularly limited. However, it is preferably 99% by weight or less and more preferably 80% by weight or less. These alcohol concentrations are particularly preferable in a case in which the treatment reagent is in the liquid form. The treatment reagent in this embodiment is more preferably an aqueous solution containing an alkaline substance in an amount that accounts for 0.1% by weight or more and a thiol reductant in an amount 0.5% by weight or more with respect to the total amount of the treatment reagent and it is further preferably an aqueous solution further containing alcohol in an amount that accounts for 20% by weight with respect to the total amount of the treatment reagent. The still more preferable range of the concentration of each component is described above. The treatment reagent in this embodiment may further contain another component other than the above components. Another component is preferably a chaotropic agent. The amount of a chaotropic agent is preferably an amount such that the final concentration of the chaotropic agent when mixed with a specimen is within the above scope.

The treatment reagent in this embodiment, which contains the component for reducing infectivity of a microorganism, the component for causing a nucleic acid to be released, and a thiol reductant, can exhibit the following four advantageous effects: (1) reducing viscosity of a highly viscous specimen containing a component crosslinked by an S—S bond, such as sputum; (2) facilitating silica to adsorb a nucleic acid; (3) sterilizing; and (4) extracting a nucleic acid from a microorganism or other cells (e.g., human cells in a specimen) in a specimen. Therefore, in a case in which a nucleic acid from a microorganism or other cells is separated from a highly viscous specimen such as sputum, it is only required to mix the treatment reagent in this embodiment with the specimen and bring the thus formed mixture into contact with a carrier comprising silica, which is a convenient operation. With the use of the treatment reagent in this embodiment, there is no need to carry out pretreatment for reducing viscosity of a specimen and treatment for extracting a nucleic acid as separate steps. In addition, in the above method for collecting a nucleic acid by allowing silica to adsorb the nucleic acid released in a mixture, the nucleic acid is concentrated through adsorption by silica, which results in an increased nucleic acid collection rate. As a method for collecting a nucleic acid from a sample containing a nucleic acid and impurities, a conventional method, in which a sample containing a nucleic acid and impurities is allowed to pass through zeolite such that the impurities are removed when adsorbed by zeolite, thereby collecting the nucleic acid that has passed through zeolite, has been known. However, nucleic acid cannot be concentrated in this method, which results in a low nucleic acid collection rate. In addition, as a specimen treatment method for reducing viscosity of a sputum specimen, the NALC (N-acetyl-L-cysteine)-NaOH method has been known as a conventional method. However, since the NALC-NaOH method is used in a test of culturing or smearing a treated specimen, the above effects (3) and (4) cannot be obtained. Conventional methods of subjecting a microorganism in a highly viscous specimen such as sputum to a nucleic acid test comprise a step of reducing viscosity of a specimen by the NALC-NaOH method and a step of extracting a nucleic acid in a specimen by heat extraction or the like, indicating that the operations are very complicated.

In addition, a method comprising treating a specimen with the treatment reagent in this embodiment, bringing a mixture, in which a nucleic acid present in the specimen has been released, into contact with a nucleic acid adsorptive carrier, and collecting the nucleic acid by allowing the carrier to adsorb the nucleic acid is effective for concentration of the nucleic acid, which results in a high nucleic acid collection rate. This is particularly effective for nucleic acid extraction from a specimen having a low nucleic acid concentration (or a low cell concentration). Therefore, it becomes possible to concentrate a nucleic acid in a specimen, from which a nucleic acid could not be detected in pretreatment by a nucleic acid amplification method according to conventional methods (the method using zeolite and the NALC-NaOH method), at a detectable concentration and collecting the nucleic acid by extraction. In addition, in the above method comprising collecting a nucleic acid by allowing a carrier to adsorb the nucleic acid, it is possible to wash the carrier with a substance that does not elute a nucleic acid after allowing the carrier to adsorb the nucleic acid. In this case, impurities other than a nucleic acid can be removed. Impurities other than a nucleic acid such as proteins, lipids, and polysaccharides are known to negatively affect a nucleic acid amplification reaction. In particular, in a case in which a nucleic acid to be amplified is present in a small amount in a specimen, inhibition of amplification might cause the amount of the amplied products to remain below the detection sensitivity. Therefore, detection performance of a nucleic acid amplification method can be improved by removing impurities.

<Preferable Embodiment of the Nucleic Acid Separation Method of the Present Invention>

Another embodiment of the present invention relates to a method for separating a nucleic acid from a specimen containing a nucleic acid and a component crosslinked by an S—S bond, which comprises allowing a nucleic acid released from the specimen to be adsorbed by a carrier in the presence of a mixture of a treatment reagent containing the component for reducing infectivity of a microorganism, the component for causing a nucleic acid to be released, and a thiol reductant and the specimen.

As the component for reducing infectivity of a microorganism and the component for causing a nucleic acid to be released, a component that can reduce infectivity of a microorganism and also can cause a nucleic acid to be released may be used.

Usually, a specimen comprising a component crosslinked by an S—S bond, such as sputum, has high viscosity and low fluidity. However, fluidity can be improved by mixing the treatment reagent containing a thiol reductant with the specimen. In addition, in a mixture of the treatment reagent and the specimen, infectivity of the specimen is reduced and the release of a nucleic acid is promoted. The nucleic acid released from the specimen is adsorbed by the carrier by bringing the mixture into contact with the carrier.

In the method in this embodiment, as described above, a nucleic acid released from a specimen in the mixture is adsorbed by the carrier so as to be concentrated, which results in a high nucleic acid collection rate. Therefore, a nucleic acid can be collected from a specimen, from which it is impossible to collect a nucleic acid by conventional methods because of a low nucleic acid concentration.

It is preferable to bring the mixture into contact with the carrier several minutes, e.g., 3 to 7 minutes, after mixing in order to allow a nucleic acid to be sufficiently released from the specimen. It is possible to bring the mixture into contact with the carrier at room temperature, e.g., 20° C. to 30° C.

The carrier preferably contains silica in the method in this embodiment. A specific embodiment of the carrier containing silica is described in <Carrier that adsorbs nucleic acid> described above. A carrier containing silica has relatively high liquid permeability. It is therefore easy to allow the mixture to permeate through the carrier by a small pressure difference that can be generated manually. It is therefore possible to manually allow the mixture to permeate through the carrier when bringing the mixture into contact with the carrier.

In the method of this embodiment, a method comprising allowing the carrier to adsorb a nucleic acid so as to collect the nucleic acid from the carrier is not particularly limited. For example, after allowing the carrier to adsorb a nucleic acid, the carrier adsorbing the nucleic acid is washed with a washing liquid, and then, it is brought into contact with an eluent for eluting a nucleic acid, thereby allowing the nucleic acid to be eluted from the carrier so as to collect the nucleic acid. Specific embodiments of the washing liquid and the eluent are described in <Washing liquid> and <Eluent> described above.

A specific embodiment of the treatment reagent used in the method in this embodiment, which contains the component for reducing infectivity of a microorganism, the component for causing a nucleic acid to be released, and a thiol reductant, is described above. More preferably, the treatment reagent contains an alcohol, an alkaline substance, and a thiol reductant.

The method in this embodiment encompasses a method for separating a nucleic acid from the specimen using the carrier that is contained in the device of the present invention and a method for separating a nucleic acid from the specimen using the carrier that is not contained in the device of the present invention. The expression "device of the present invention" refers to a "device for separating a nucleic acid from a specimen containing a nucleic acid by bringing a mixture of a specimen containing a nucleic acid and a treatment reagent for causing a nucleic acid in a specimen to be released into contact with a carrier that adsorbs a nucleic acid, which includes: a treatment reagent-accommodating container configured to have an inner container space, the volume of which can be reduced, the container accommodating a treatment reagent for causing a nucleic acid in a specimen to be released in the inner container space and having a discharging opening for releasing the treatment reagent; and a nucleic acid-collecting member configured to have an accommodation space for accommodating a specimen, in which a treatment reagent-supplying opening is formed on one side of the accommodation space so as to be connected to the treatment reagent-accommodating container, thereby allowing the treatment reagent to be supplied, and a mixture-discharging opening is formed on the other side of the accommodation space so as to discharge the mixture via a carrier that adsorbs a nucleic acid released in the mixture while allowing the mixture to permeate therethrough, wherein the device is configured such that a cover for sealing the discharging opening is attached to the discharging opening of the treatment reagent-accommodating container, and wherein the nucleic acid-collecting member allows the discharging opening sealed with the cover to be opened, thereby causing the discharging opening to be communicated with the treatment reagent-supplying opening, when the treatment reagent-accommodating container is connected to the treatment reagent-supplying opening of the nucleic acid-collecting member" described herein or in the claims or a preferable embodiment thereof.

EXAMPLES

The present invention is specifically described with reference to the Examples below. However, the present invention is not limited to these Examples.

Example 1

The operations described below were carried out using a treatment reagent-accommodating container 100, a nucleic acid-collecting member 200, a discharged matter-accommodating container 400, a washing liquid-accommodating container 440, a connecting member 450, an eluent-accommodating container 460, and a nucleic acid-collecting container 470 as illustrated in the figures. The nucleic acid-collecting member 200 is prepared by combining a specimen-receiving member 240 and a carrier-holding member 250 as illustrated in FIG. 2. The carrier-holding member 250 comprises a circular membrane-like carrier formed with silica monolith having nucleic acid adsorption ability (membrane thickness: 1.5 mm; aperture: 4 mm; through-pore diameter: 30 to 40 µm (measurement method: the mean value calculated based on a scanning electron microscope image)) serving as a carrier 205. Note that a deformable bag-shaped container that allows a pressure-feeding unit 461 to be squeezed, thereby reducing the volume of a pressure-feeding unit inner space 111 and the volume of an inner container space 110, which differs from the embodiment illustrated in FIG. 4E, was used as the eluent-accommodating container 460.
(Nucleic Acid Extraction)

As illustrated in FIG. 4A, a nucleic acid-collecting member 200 was connected to a discharged matter-accommodating container 400, and then, 3 mL of a culture suspension of *Mycobacterium smegmatis* (*M. smegmatis*) known as an acid-fast bacterium ($1.0 \times 10^6$ CFU/mL) was introduced as a specimen S into an accommodation space 203 of the nucleic acid-collecting member 200. Next, as illustrated in FIG. 4B, a treatment reagent-accommodating container 100, in which 5 mL of an aqueous solution containing 5% by weight sodium hydroxide and 60% by weight ethanol was enclosed as a treatment reagent 101, was connected to the nucleic acid-collecting member 200. Subsequently, the specimen S and the treatment reagent 101 were mixed in a mixing space 420 by shaking the device as a whole 10 times in a vertical direction, thereby obtaining a mixture 421. Then, the mixture was allowed to stand still at room temperature for 5 minutes.

As illustrated in FIG. 4C, a pressure-feeding unit 103 having an accordion structure of the treatment reagent-accommodating container 100 was squeezed, thereby allowing the mixture 421 to pass through the carrier 205. The unwashed carrier 205 adsorbing a nucleic acid was designated as carrier 205'. The treatment reagent-accommodating container 100 and the specimen-receiving member 240 of the nucleic acid-collecting member 200 were removed at the same time. Then, as illustrated in FIG. 4D, the washing liquid-accommodating container 440, in which 15 mL of a 40% by weight ethanol aqueous solution was enclosed as a washing liquid 443, was connected to the carrier-holding member 250 via the connecting member 450. Subsequently, a pressure-feeding unit 441 having an accordion structure of the washing liquid-accommodating container 440 was squeezed, thereby allowing the washing liquid 443 to pass through the carrier 205'. Then, after the pressure-feeding unit 441 returned to the original shape, the pressure-feeding unit 441 was squeezed again, thereby allowing the air inside the washing liquid-accommodating container 440 to pass through the carrier 205'. The washed carrier 205 adsorbing a nucleic acid was designated as carrier 205". The washing liquid-accommodating container 440 was removed. As illustrated in FIG. 4E, the eluent-accommodating container 460, in which water was enclosed as an eluent 463, was connected to the carrier-holding member 250 via the connecting member 450. In addition, the discharged matter-accommodating container 400 was removed and the nucleic acid-collecting container 470 was connected to the carrier-holding member 250. The above-described bag-shaped container constituting a pressure-feeding unit 461 of the eluent-accommodating container 460 was squeezed, thereby allowing the eluent 463 to pass through the carrier 205" and recovering the eluent into the nucleic acid-collecting container 470. The eluent 463 that had permeated through the carrier 205" was collected in an amount of 10 µL and amplified by real-time PCR, followed by detection. Thus, extraction of the nucleic acid of *M. smegmatis* was confirmed. The time required for nucleic acid extraction and purification excluding the time required for PCR was approximately 7 minutes.

Example 2

The nucleic acid was purified, amplified by real-time PCR, and detected, thereby confirming extraction of the nucleic acid of *M. smegmatis*, in the same manner as in Example 1 except that a culture suspension of *M. smegmatis* ($1.0 \times 10^4$ CFU/mL) was used as a specimen S. The time required for nucleic acid extraction and purification excluding the time required for PCR was approximately 7 minutes.

Example 3

The nucleic acid was purified, amplified by real-time PCR, and detected, thereby confirming extraction of the nucleic acid of *M. smegmatis*, in the same manner as in Example 1 except that a culture suspension of *M. smegmatis* ($1.0 \times 10^2$ CFU/mL) was used as a specimen S. The time required for nucleic acid extraction and purification excluding the time required for PCR was approximately 7 minutes.

Example 4

The nucleic acid was purified, amplified by real-time PCR, and detected, thereby confirming extraction of the nucleic acid of *M. smegmatis*, in the same manner as in Example 1 except that a washing liquid-accommodating container 440, in which 15 mL of a 60% by weight ethanol aqueous solution was enclosed as the washing liquid 443, was used. The time required for nucleic acid extraction and purification excluding the time required for PCR was approximately 7 minutes.

Example 5

The nucleic acid was purified, amplified by real-time PCR, and detected, thereby confirming extraction of the nucleic acid of *M. smegmatis*, in the same manner as in Example 1 except that a washing liquid-accommodating container 440, in which 15 mL of a 20% by weight ethanol aqueous solution was enclosed as the washing liquid 443, was used. The time required for nucleic acid extraction and purification excluding the time required for PCR was approximately 7 minutes.

Example 6

The nucleic acid was purified, amplified by real-time PCR, and detected, thereby confirming extraction of the nucleic acid of *M. smegmatis*, in the same manner as in Example 1 except that a treatment reagent-accommodating container 100, in which 3 mL of an aqueous solution containing 5% by weight sodium hydroxide and 60% by weight ethanol was enclosed as the treatment reagent 101, was used. The time required for nucleic acid extraction and purification excluding the time required for PCR was approximately 7 minutes.

Example 7

The nucleic acid was purified, amplified by real-time PCR, and detected, thereby confirming extraction of the nucleic acid of *M. smegmatis*, in the same manner as in Example 1 except that a treatment reagent-accommodating container 100, in which 15 mL of an aqueous solution containing 5% by weight sodium hydroxide and 60% by weight ethanol was enclosed as the treatment reagent 101, was used. The time required for nucleic acid extraction and purification excluding the time required for PCR was approximately 7 minutes.

Example 8

The nucleic acid was purified, amplified by real-time PCR, and detected, thereby confirming extraction of the nucleic acid of *M. smegmatis*, in the same manner as in Example 1 except that a treatment reagent-accommodating container 100, in which 5 mL of an aqueous solution containing 5% by weight sodium hydroxide, 30% by weight sodium iodide (at a final concentration of approximately 1.3 M when mixed with a specimen), and 60% by weight ethanol was enclosed as the treatment reagent 101, was used. The time required for nucleic acid extraction and purification excluding the time required for PCR was approximately 7 minutes.

Example 9

The nucleic acid was purified, amplified by real-time PCR, and detected, thereby confirming extraction of the nucleic acid of *M. smegmatis*, in the same manner as in Example 1 except that a treatment reagent-accommodating container 100, in which 5 mL of an aqueous solution containing 5% by weight sodium hydroxide, 20% by weight sodium iodide (at a final concentration of approximately 0.8 M when mixed with a specimen), and 60% by weight ethanol was enclosed as the treatment reagent 101, was used. The time required for nucleic acid extraction and purification excluding the time required for PCR was approximately 7 minutes.

Example 10

The nucleic acid was purified, amplified by real-time PCR, and detected, thereby confirming extraction of the nucleic acid of *M. smegmatis*, in the same manner as in Example 1 except that a treatment reagent-accommodating container 100, in which 5 mL of an aqueous solution containing 5% by weight sodium hydroxide, 20% by weight urea (at a final concentration of approximately 2.1 M when mixed with a specimen), and 60% by weight ethanol was enclosed as the treatment reagent 101, was used. The time required for nucleic acid extraction and purification excluding the time required for PCR was approximately 7 minutes.

Example 11

The nucleic acid was purified, amplified by real-time PCR, and detected, thereby confirming extraction of the nucleic acid of *M. smegmatis* in the same manner as in Example 1 except that a carrier having a membrane thickness of 1.0 mm, an aperture of 4 mm, and a through-pore diameter of 30 to 40 µm (measurement method: the mean value calculated based on a scanning electron microscope image) was used as the circular membrane-like carrier formed with silica monolith having nucleic acid adsorption ability. The time required for nucleic acid extraction and purification excluding the time required for PCR was approximately 7 minutes.

Example 12

The nucleic acid was purified, amplified by real-time PCR, and detected, thereby confirming extraction of the nucleic acid of *M. smegmatis* in the same manner as in Example 1 except that a carrier having a membrane thickness of 1.5 mm, an aperture of 10 mm, and a through-pore diameter of 30 to 40 µm (measurement method: the mean value calculated based on a scanning electron microscope image) was used as the circular membrane-like carrier formed with silica monolith having nucleic acid adsorption ability. The time required for nucleic acid extraction and purification excluding the time required for PCR was approximately 7 minutes.

Example 13

The nucleic acid was purified, amplified by real-time PCR, and detected, thereby confirming extraction of the nucleic acid of *M. smegmatis* in the same manner as in Example 1 except that a carrier having a membrane thickness of 1.0 mm, an aperture of 4 mm, and a through-pore diameter of 5 to 10 µm (measurement method: the mean value calculated based on a scanning electron microscope image) was used as the circular membrane-like carrier formed with silica monolith having nucleic acid adsorption ability. The time required for nucleic acid extraction and purification excluding the time required for PCR was approximately 7 minutes.

The real-time PCR primers used for detecting the nucleic acid of M. smegmatis in Examples 1 to 13 were as follows: a forward primer/5'-ACATGCAAGTCGAACGGAAA-3') (SEQ ID NO: 1); and a reverse primer/(5'-CCCAC-CAACAAGCTGATAGG-3') (SEQ ID NO: 2). The real-time PCR reagent used herein was polymerase TAKARA Taq HS manufactured by Takara Bio Inc. Real-time PCR was performed with the addition of SYBR Green I (Lonza) diluted at a final concentration of 1/20000. The reaction was incubated using a Light Cycler 96 System (Roche) at 98° C./1 minute, followed by 40 PCR cycles of 98° C./10 seconds→60° C./10 seconds→72° C./10 seconds. The nucleic acid amplification reaction was monitored.

Example 14

The operations described below were carried out using a treatment reagent-accommodating container 100, a nucleic acid-collecting member 200, a discharged matter-accommodating container 400, a washing liquid-accommodating container 440, a connecting member 450, an eluent-accommodating container 460, and a nucleic acid-collecting container 470 as illustrated in the figures. The nucleic acid-collecting member 200 is prepared by combining a specimen-receiving member 240 and a carrier-holding member 250 as illustrated in FIG. 2. The carrier-holding member 250 comprises a circular membrane-like carrier formed with silica monolith having nucleic acid adsorption ability (membrane thickness: 1.5 mm; aperture: 4 mm; through-pore diameter: 30 to 40 µm (measurement method: the mean value calculated based on a scanning electron microscope image)) serving as a carrier 205. Note that a deformable bag-shaped container that allows a pressure-feeding unit 461 to be squeezed, thereby reducing the volume of a pressure-feeding unit inner space 111 and the volume of an inner container space 110, which differs from the embodiment illustrated in FIG. 4E, was used as the eluent-accommodating container 460.

As illustrated in FIG. 4A, the nucleic acid-collecting member 200 was connected to the discharged matter-accommodating container 400, and then, 3 mL of a culture suspension of M. bovis (BCG strain) known as a tuberculosis bacterium ($1.0 \times 10^4$ CFU/mL) was introduced as a specimen S into an accommodation space 203 of the nucleic acid-collecting member 200. Next, as illustrated in FIG. 4B, a treatment reagent-accommodating container 100, in which 5 mL of an aqueous solution containing 5% by weight sodium hydroxide and 60% by weight ethanol was enclosed as a treatment reagent 101, was connected to the nucleic acid-collecting member 200. Subsequently, the specimen S and the treatment reagent 101 were mixed in a mixing space 420 by shaking the device as a whole 10 times in a vertical direction, thereby obtaining a mixture 421. Then, the mixture was allowed to stand still at room temperature for 5 minutes.

As illustrated in FIG. 4C, a pressure-feeding unit 103 having an accordion structure of the treatment reagent-accommodating container 100 was squeezed, thereby allowing the mixture 421 to pass through the carrier 205. The unwashed carrier 205 adsorbing a nucleic acid was designated as carrier 205'. The treatment reagent-accommodating container 100 and the specimen-receiving member 240 of the nucleic acid-collecting member 200 were removed at the same time. Then, as illustrated in FIG. 4D, the washing liquid-accommodating container 440, in which 15 mL of a 40% by weight ethanol aqueous solution was enclosed as a washing liquid 443, was connected to the carrier-holding member 250 via the connecting member 450. Subsequently, a pressure-feeding unit 441 having an accordion structure of the washing liquid-accommodating container 440 was squeezed, thereby allowing the washing liquid 443 to pass through the carrier 205'. Then, after the pressure-feeding unit 441 returned to the original shape, the pressure-feeding unit 441 was squeezed again, thereby allowing the air inside the washing liquid-accommodating container 440 to pass through the carrier 205'. The washed carrier 205 adsorbing a nucleic acid was designated as carrier 205''. The washing liquid-accommodating container 440 was removed. As illustrated in FIG. 4E, the eluent-accommodating container 460, in which water was enclosed as an eluent 463, was connected to the carrier-holding member 250 via the connecting member 450. In addition, the discharged matter-accommodating container 400 was removed and the nucleic acid-collecting container 470 was connected to the carrier-holding member 250. The above-described bag-shaped container constituting a pressure-feeding unit 461 of the eluent-accommodating container 460 was squeezed, thereby allowing an eluent 463 to pass through the carrier 205'' and recovering the eluent into a nucleic acid-collecting container 470. The eluent 463 that had permeated through the carrier 205'' was collected in an amount of 10 µL and amplified by real-time PCR, followed by detection. Thus, extraction of the nucleic acid of M. Bovis was confirmed. The time required for nucleic acid extraction and purification excluding the time required for PCR was approximately 7 minutes.

Example 15

The nucleic acid was purified, amplified by real-time PCR, and detected, thereby confirming extraction of the nucleic acid of M. bovis (BCG strain) in the same manner as in Example 14, except that a culture suspension of M. bovis ($1.0 \times 10^2$ CFU/mL) was used as a specimen S. The time required for nucleic acid extraction and purification excluding the time required for PCR was approximately 7 minutes.

Example 16

The nucleic acid was purified, amplified by real-time PCR, and detected, thereby confirming extraction of the nucleic acid of M. bovis (BCG strain) in the same manner as in Example 14, except that a culture suspension of M. bovis ($5.0 \times 10^1$ CFU/mL) was used as a specimen S. The time required for nucleic acid extraction and purification excluding the time required for PCR was approximately 7 minutes.

Example 17

The nucleic acid was purified, amplified by real-time PCR, and detected, thereby confirming extraction of the nucleic acid of M. bovis (BCG strain) in the same manner as in Example 14 except that a culture suspension of M. bovis ($2.5 \times 10^1$ CFU/mL) was used as a specimen S. The time required for nucleic acid extraction and purification excluding the time required for PCR was approximately 7 minutes.

Example 18

The nucleic acid was purified, amplified by real-time PCR, and detected, thereby confirming extraction of the nucleic acid of M. bovis (BCG strain) in the same manner as in Example 14 except that a viscous solution prepared by adding porcine-derived mucin to a culture suspension of *M. bovis* (5.0×10$^1$ CFU/mL) so as to result in a concentration of 20% by weight was used as a specimen S, and the treatment reagent-accommodating container 100, in which 5 mL of an aqueous solution containing 5% by weight sodium hydroxide, 5% by weight N-acetyl-L-cysteine, and 60% by weight ethanol was enclosed as the treatment reagent 101, was used. The time required for nucleic acid extraction and purification excluding the time required for PCR was approximately 7 minutes.

Example 19

The nucleic acid was purified, amplified by real-time PCR, and detected, thereby confirming extraction of the nucleic acid of *Escherichia coli* (*E. Coli*) in the same manner as in Example 14 except that a culture suspension of *E. coli* ($1.0\times10^2$ CFU/mL) was used as a specimen S. The time required for nucleic acid extraction and purification excluding the time required for PCR was approximately 7 minutes.

Example 20

The nucleic acid was purified, amplified by real-time PCR, and detected, thereby confirming extraction of the nucleic acid of *Streptococcus thermophilus* (*S. thermophilus*), in the same manner as in Example 14 except that a culture suspension of *S. thermophilus* ($1.0\times10^2$ CFU/mL) was used as a specimen S. The time required for nucleic acid extraction and purification excluding the time required for PCR was approximately 7 minutes.

Example 21

(Test of Disinfecting Ability)

In this Example, a treatment reagent used in a nucleic acid separation device was evaluated in terms of ability to disinfect *M. smegmatis* and *M. bovis* BCG (BCG).

<Preparation of Bacterial Suspension>

*M. smegmatis* was cultured using a liquid medium for proliferating acid-fast bacteria (manufactured by Kyokuto Pharmaceutical Industrial Co., Ltd.) at 37° C. for 2 weeks. The culture suspension was filtered through an Acrodisk filter (manufactured by Pall Corporation) having a pore size of 5 μm, thereby removing unnecessary mass. The filtrate was subjected to measurement at an absorbance of 530 nm, and the filtrate was confirmed to have an O.D. of 0.1. The filtrate was used as a bacterial suspension containing $10^7$ cells/ml for evaluation of disinfecting ability described below.

In addition, a mixture was prepared by mixing the above-described bacterial suspension and a porcine stomach-derived mucin powder (manufactured by Sigma-Aldrich) so as to result in a mucin concentration of 20% by weight.
The resulting mixture was used as artificial sputum of *M. smegmatis* having sputum-like fluidity for evaluation of disinfecting ability described below.

BCG was also cultured in a liquid medium similar to that used for *M. smegmatis* for 3 weeks. A BCG suspension and artificial sputum of BCG for evaluation of disinfecting ability were prepared in the same manner as in the above case of the bacterial suspension and artificial sputum of *M. smegmatis.*

<Preparation of Treatment Reagent>

A composition obtained by mixing two components i.e., ethanol (EtOH) and sodium hydroxide (NaOH), a composition obtained by mixing three components, i.e., these two components and N-acetyl-L-cysteine (NALC), and a composition obtained by mixing these three components and glutaraldehyde were prepared as treatment reagents used for the evaluation. In addition, a phenol solution was used as a positive control (PC), and physiological saline was used as a negative control (NC). Table 1 lists the compositions of the treatment reagents used for the evaluation. In table 1, each composition is in the form of an aqueous solution, and the proportion of each component of the composition is expressed in % by weight.

TABLE 1

| | Treatment reagent composition |
|---|---|
| Composition 1 | 60% EtOH + 5% NaOH |
| Composition 2 | 60% EtOH + 5% NaOH + 5% NALC |
| Composition 3 | 60% EtOH + 5% NaOH + 5% NALC + 3.5% Glutaraldehyde |
| Composition 4 | 5% Phenol (positive control) |
| Composition 5 | Physiological saline (negative control) |

<Evaluation of Disinfecting Ability>

The disinfecting ability of each treatment reagent was evaluated using the four types of preparations, i.e., the *M. smegmatis* suspension, the BCG suspension, the artificial sputum containing *M. smegmatis*, and the artificial sputum containing BCG described above.

Each of the suspensions of *M. smegmatis* and BCG (500 μL) was mixed with 250 to 1500 μL of each of the treatment reagents listed in Table 1, followed by inversion mixing. Each mixture was allowed to stand still at room temperature for 5 minutes. Thereafter, in order to remove the treatment reagent, each mixture was centrifuged (5600 rpm, 4° C., 20 minutes), and the supernatant was removed and replaced by physiological saline. In the culture described below, centrifugation and replacement by physiological saline were repeated three times in order to avoid the influence of bacteriostasis of the treatment reagent.

After the above procedure was repeated three times, physiological saline was used for preparing a dilution series (up to 105-fold dilution). Each dilution was seeded on a 7H11C agar medium (manufactured by Kyokuto Pharmaceutical Industrial Co., Ltd.), followed by culture at 37° C. The viable cell count (microbial colony count) was determined. Based on the obtained viable cell count, the disinfection rate was calculated as an index for disinfection efficacy. The disinfection rate was calculated by the following formula.

$$\text{Disinfection rate (\%)}=[(\text{NC viable cell count})-(\text{viable cell count when using a treatment reagent})]/(\text{viable cell count of NC})\times100$$

Artificial sputum of *M. smegmatis* and artificial sputum of BCG were also evaluated in terms of disinfection efficacy in the same manner as in the case of the above evaluation of bacterial suspensions. Accordingly, the disinfection rates were calculated.

Table 2 list the evaluation results. If the calculated disinfection rate reached 99.99999%, the corresponding reagent was regarded as having an effective chemical composition of a treatment reagent used for a nucleic acid separation device. In the table below, symbol "O" may be expressed as "A" and symbol "x" may be expressed as "B."

TABLE 2

| Treatment reagent | Amount of treatment reagent used | Suspension of M. smegmatis | Artificial sputum + Suspension of M. smegmatis | Suspension of BCG strain | Artificial sputum + Suspension of BCG strain |
|---|---|---|---|---|---|
| Composition 1 | 500 μL | ○ | — | ○ | — |
| Composition 2 | 250 μL | ○ | ○ | ○ | X |
| Composition 2 | 1000 μL | — | — | — | ○ |
| Composition 2 | 1500 μL | — | — | — | ○ |
| Composition 3 | 500 μL | ○ | ○ | ○ | ○ |
| Composition 4 | 500 μL | ○ | ○ | ○ | ○ |
| Composition 5 | 500 μL | X | X | X | X |

*In the table, symbol "○" indicates that the disinfection rate reached 99.99999%, symbol "X" indicates that the disinfection rate did not reach 99.99999%, and symbol "—" indicates that the corresponding reagent was not tested.

It was confirmed that 99.99999% of *M. smegmatis* and BCG contained in a bacterial suspension or artificial sputum can be disinfected with the use of the treatment reagents used in the evaluation above.

Example 22

The nucleic acid was purified, amplified by real-time PCR, and detected, thereby confirming extraction of the nucleic acid of *M. bovis*, in the same manner as in Example 1 except that a mixture prepared by adding 3 μL of a culture suspension of *M. bovis* ($1.0 \times 10^7$ CFU/mL) to 3 mL of murine blood and sufficiently mixing the resulting mixture was used as a specimen S. The time required for nucleic acid extraction and purification excluding the time required for PCR was approximately 7 minutes.

Example 23

The nucleic acid was purified, amplified by real-time PCR, and detected, thereby confirming extraction of the nucleic acid of *M. bovis*, in the same manner as in Example 1 except that a mixture prepared by adding 3 μL of a culture suspension of *M. bovis* ($1.0 \times 10^7$ CFU/mL) to 3 cc of ground murine muscle tissue and sufficiently mixing the resulting mixture was used as a specimen S. The time required for nucleic acid extraction and purification excluding the time required for PCR was approximately 7 minutes.

Example 24

The nucleic acid was purified, amplified by real-time PCR, and detected, thereby confirming extraction of the nucleic acid of *M. bovis*, in the same manner as in Example 1 except that a mixture prepared by adding 3 μL of a culture suspension of *M. bovis* ($0.5 \times 10^5$ CFU/mL) to 3 mL of a culture suspension of *E. coli* ($1.0 \times 10^7$ CFU/mL) and sufficiently mixing the resulting mixture was used as a specimen S. The time required for nucleic acid extraction and purification excluding the time required for PCR was approximately 7 minutes.

Example 25

The nucleic acid was purified, amplified by real-time PCR, and detected, thereby confirming extraction of the nucleic acid of the tuberculosis complex in the same manner as in Example 14 except that sputum (smear test: 2+; culture test: positive) was used as a specimen S, and the treatment reagent-accommodating container 100, in which 5 mL of an aqueous solution comprising 5% by weight sodium hydroxide, 5% by weight N-acetyl-L-cysteine, and 60% by weight ethanol was enclosed as the treatment reagent 101, was used. The time required for nucleic acid extraction and purification excluding the time required for PCR was approximately 7 minutes.

The term "smear test" used herein refers to a method for confirming the presence or absence of acid-fast bacteria by pretreatment, dyeing, and microscopic examination of sputum according to the smear test method described in "Tubercle *Bacillus* 2007" (published by Japan Anti Tuberculosis Association). Collected sputum was mixed with two times its volume of an NALC-NaOH reagent (BD Myco-Prep, manufactured by Nippon Becton Dickinson and Company, Ltd.) and stirred by a vortex mixer. A 0.07 M sterile phosphate buffer solution was added such that the total volume was adjusted to 50 mL, followed by centrifugation at 3000 g for 20 minutes. The supernatant was discarded and the precipitate was suspended in 1 mL of sterile phosphate buffer solution. The suspension in a volume of 0.05 mL was smeared on a microscope slide and air-dried. Then, the slide was passed through gas burner flame four times for fixation. The fixed smear sample was dyed in accordance with the Ziehl-Neelsen (Z-N) method and observed using an optical microscope with 1000-fold magnification. The microbial colony count in the observed visual field was recorded in accordance with the method for recording the detected microbial colony count by microscopic examination described in "Tubercle *Bacillus* 2007" (published by Japan Anti Tuberculosis Association).

The term "culture test" used herein refers to a method for confirming the occurrence or non-occurrence of proliferation of acid-fast bacteria by pretreatment, harvest, inoculation, and culture of sputum according to the isolation culture method described in "Tubercle *Bacillus* 2007" (published by Japan Anti Tuberculosis Association). An agar plate medium (Middlebrook 7H10 Agar medium) was inoculated and smeared with 0.1 mL of the suspension obtained by the same method used for the above smear test, followed by culture at 37° C. The medium was observed twice a week for 8 weeks for recording the presence or absence of colonies on the medium surface.

Example 26

The nucleic acid was extracted, purified, amplified by real-time PCR, and detected, thereby confirming extraction of the tuberculosis complex in the same manner as in Example 14 except that sputum (smear test: 1+, culture test: positive) was used as a specimen S, and the treatment reagent-accommodating solution 100, in which 5 mL of an aqueous solution containing 5% by weight sodium hydroxide, 5% by weight N-acetyl-L-cysteine, and 60% by weight ethanol was enclosed as the treatment reagent 101, was used. The time required for nucleic acid extraction and purification excluding the time required for PCR was approximately 7 minutes.

Example 27

The nucleic acid was purified, amplified by real-time PCR, and detected, thereby confirming extraction of the nucleic acid of the tuberculosis complex in the same manner as in Example 14 except that sputum (smear test: ±; culture test: positive) was used as a specimen S, and the treatment reagent-accommodating container 100, in which 5 mL of an aqueous solution containing 5% by weight sodium hydroxide, 5% by weight N-acetyl-L-cysteine, and 60% by weight ethanol was enclosed as the treatment reagent 101, was used. The time required for nucleic acid extraction and purification excluding the time required for PCR was approximately 7 minutes.

Example 28

The nucleic acid was purified, amplified by real-time PCR, and detected, thereby confirming extraction of the nucleic acid of the tuberculosis complex in the same manner as in Example 14 except that sputum (smear test: −; culture test: positive) was used as a specimen S, and the treatment reagent-accommodating container 100, in which 5 mL of an aqueous solution containing 5% by weight sodium hydroxide, 5% by weight N-acetyl-L-cysteine, and 60% by weight ethanol was enclosed as the treatment reagent 101, was used. The time required for nucleic acid extraction and purification excluding the time required for PCR was approximately 7 minutes.

Example 29

The nucleic acid was purified, amplified by real-time PCR, and detected, thereby confirming extraction of the nucleic acid of the tuberculosis complex in the same manner as in Example 14 except that a 10-fold dilution of sputum (smear test: −; culture test: positive) was used as a specimen S, and the treatment reagent-accommodating container 100, in which 5 mL of an aqueous solution containing 5% by weight sodium hydroxide, 5% by weight N-acetyl-L-cysteine, and 60% by weight ethanol was enclosed as the treatment reagent 101, was used. The time required for nucleic acid extraction and purification excluding the time required for PCR was approximately 7 minutes.

Example 30

The nucleic acid was purified, amplified by real-time PCR, and detected, thereby confirming extraction of the nucleic acid of the tuberculosis complex in the same manner as in Example 14 except that a 100-fold dilution of sputum (smear test: −; culture test: positive) was used as a specimen S, and the treatment reagent-accommodating container 100, in which 5 mL of an aqueous solution containing 5% by weight sodium hydroxide, 5% by weight N-acetyl-L-cysteine, and 60% by weight ethanol was enclosed as the treatment reagent 101, was used. The time required for nucleic acid extraction and purification excluding the time required for PCR was approximately 7 minutes.

Example 31

The nucleic acid was purified, amplified by real-time PCR, and detected, thereby confirming extraction of the nucleic acid of the tuberculosis complex in the same manner as in Example 14 except that a 1000-fold dilution of sputum (smear test: −; culture test: positive) was used as a specimen S, and the treatment reagent-accommodating container 100, in which 5 mL of an aqueous solution containing 5% by weight sodium hydroxide, 5% by weight N-acetyl-L-cysteine, and 60% by weight ethanol was enclosed as the treatment reagent 101, was used. The time required for nucleic acid extraction and purification excluding the time required for PCR was approximately 7 minutes.

Comparative Example 1

Nucleic acid extraction was performed using, as a specimen, a culture suspension of a tuberculosis bacterium, i.e., $M.$ $Bovis$ (BCG strain) ($1.0 \times 10^4$ CFU/mL) and a Loopamp (registered trademark) PURE DNA Extraction Kit marketed by Eiken Chemical Co., Ltd. in accordance with the instruction manual for the kit. The culture suspension in a volume of 60 μL was added to a specimen treatment tube and heated at 90° C. for 5 minutes and left at room temperature for 2 minutes. An adsorbent tube was connected to the specimen treatment tube, followed by mixing by shaking in vertical and horizontal directions. An instillation injection cap was connected thereto. The adsorbent tube was squeezed to collect a nucleic acid extraction liquid. The collected nucleic acid extraction liquid was sampled in an amount of 10 μL and amplified by real-time PCR, and detected, thereby confirming extraction of the nucleic acid of $M.$ $Bovis$. The time required for nucleic acid extraction and purification excluding the time required for PCR was approximately 9 minutes.

Comparative Example 2

The nucleic acid was purified, amplified by real-time PCR, and detected, thereby confirming extraction of the nucleic acid of $M.$ $bovis$ in the same manner as in Comparative Example 1 except that a culture suspension of $M.$ $bovis$ (BCG strain) ($1.0 \times 10^2$ CFU/mL) was used as a specimen. The time required for nucleic acid extraction and purification excluding the time required for PCR was approximately 9 minutes.

Comparative Example 3

The nucleic acid was purified, amplified by real-time PCR, and detected, thereby confirming extraction of the nucleic acid of $M.$ $bovis$ in the same manner as in Comparative Example 1 except that a culture suspension of $M.$ $bovis$ (BCG strain) ($5.0 \times 10^1$ CFU/mL) was used as a specimen. The time required for nucleic acid extraction and purification excluding the time required for PCR was approximately 9 minutes.

Comparative Example 4

The nucleic acid was purified, amplified by real-time PCR, and detected in the same manner as in Comparative Example 1 except that a culture suspension of $M.$ $bovis$ (BCG strain) ($2.5 \times 10^1$ CFU/mL) was used as a specimen. Accordingly, nucleic acid amplification was not detected by real-time PCR.

Comparative Example 5

The nucleic acid was purified, amplified by real-time PCR, and detected in the same manner as in Comparative Example 1 except that a viscous mixture prepared by adding porcine-derived mucin to a culture suspension of *M. bovis* (BCG strain) ($1.0 \times 10^3$ CFU/mL) so as to result in a concentration of 20% by weight was used as a specimen. Accordingly, nucleic acid amplification was not detected by real-time PCR.

Comparative Example 6

The nucleic acid was purified, amplified by real-time PCR, and detected in the same manner as in Comparative Example 1 except that a viscous mixture prepared by adding porcine-derived mucin to a culture suspension of *M. bovis* (BCG strain) ($1.0 \times 10^2$ CFU/mL) so as to result in a concentration of 20% by weight was used as a specimen. Accordingly, nucleic acid amplification was not detected by real-time PCR.

Comparative Example 7

Sputum (smear test: −, culture test: positive) identical to the sputum used in Example 28 was digested and decontaminated by the NALC-NaOH method described in "Tubercle *Bacillus* 2007" (published by Japan Anti Tuberculosis Association). Subsequently, nucleic acid extraction was performed using an AMPLICOR *mycobacterium* specimen pretreatment reagent set II (manufactured by Roche Diagnostics K.K.) in accordance with the protocol described in the package insert. The obtained nucleic acid extract was amplified by real-time PCR and detected, thereby confirming nucleic acid extraction of the tuberculosis complex.

Comparative Example 8

A 100-fold dilution of sputum (smear test: −, culture test: positive) identical to the sputum used in Example 30 was digested and decontaminated by the NALC-NaOH method described in "Tubercle *Bacillus* 2007" (published by Japan Anti Tuberculosis Association). Subsequently, nucleic acid extraction was performed using an AMPLICOR *mycobacterium* specimen pretreatment reagent set II (manufactured by Roche Diagnostics K.K.) in accordance with the protocol described in the package insert. The obtained nucleic acid extract was subjected to real-time PCR. Accordingly, nucleic acid amplification was not detected.

Comparative Example 9

A 1000-fold dilution of sputum (smear test: −, culture test: positive) identical to the sputum used in Example 31 was digested and decontaminated by the NALC-NaOH method described in "Tubercle *Bacillus* 2007" (published by Japan Anti Tuberculosis Association). Subsequently, nucleic acid extraction was performed using an AMPLICOR *mycobacterium* specimen pretreatment reagent set II (manufactured by Roche Diagnostics K.K.) in accordance with the protocol described in the package insert. The obtained nucleic acid extract was subjected to real-time PCR. Accordingly, nucleic acid amplification was not detected.

Comparative Example 10

The nucleic acid was purified, amplified by real-time PCR, and detected in the same manner as in Comparative Example 1 except that sputum (smear test: −, culture test: positive) identical to the sputum used in Example 28 was used as a specimen. Accordingly, nucleic acid amplification was not detected by real-time PCR.

The real-time PCR primers used for *M. bovis* in Examples 14 to 18, 22 to 24, 32, and 33 and Comparative Examples 1 to 6 were as follows: a forward primer/5'-ACCTCACC-TATGTGTCGACC-3') (SEQ ID NO: 3); a reverse primer/(5'-AACGTCTTTCAGGTCGAGTACG-3') (SEQ ID NO: 4). The real-time PCR reagent used herein was polymerase TAKARA Taq HS manufactured by Takara Bio Inc. Real-time PCR was performed with the addition of SYBR Green I (Lonza) diluted at a final concentration of 1/20000. The reaction was incubated using a Light Cycler 96 System (Roche) at 98° C./1 minute, followed by 50 PCR cycles of 98° C./10 seconds→60° C./10 seconds→72° C./10 seconds. The nucleic acid amplification reaction was monitored.

The real-time PCR primers used for *E. coli* in Example 19 were as follows: a forward primer/5'-GGAAGAAGCTTGCTTCTTTGCTGAC-3') (SEQ ID NO: 5); a reverse primer/(5'-AGCCCGGGGATTTCA-CATCTGACTTA-3') (SEQ ID NO: 6). The real-time PCR reagent used herein was polymerase TAKARA Taq HS manufactured by Takara Bio Inc. Real-time PCR was performed with the addition of SYBR Green I (Lonza) diluted at a final concentration of 1/20000. The reaction was incubated using a Light Cycler 96 System (Roche) at 98° C./1 minute, followed by 40 PCR cycles of 98° C./10 seconds→60° C./10 seconds→72° C./10 seconds. The nucleic acid amplification reaction was monitored.

The real-time PCR primers used for detecting the nucleic acid of *S. thermophilus* in Example 20 were as follows: a forward primer/5'-GCTCCACTACAAGATGGACCTGC-3') (SEQ ID NO: 7); a reverse primer/(5'-TAG-GAGTCTGGGCCGTGTCTCAG-3') (SEQ ID NO: 8). The real-time PCR reagent used herein was polymerase TAKARA Taq HS manufactured by Takara Bio Inc. Real-time PCR was performed with the addition of SYBR Green I (Lonza) diluted at a final concentration of 1/20000. The reaction was incubated using a LightCycler96 System (Roche) at 98° C./1 minute, followed by 40 PCR cycles of 98° C./10 seconds→60° C./10 seconds→72° C./10 seconds. The nucleic acid amplification reaction was monitored.

The real-time PCR primers used for the tuberculosis complex in Examples 25 to 31 and Comparative Examples 7 to 10 were as follows: a forward primer/5'-ACCTCACC-TATGTGTCGACC-3') (SEQ ID NO: 3); a reverse primer/(5'-AACGTCTTTCAGGTCGAGTACG-3') (SEQ ID NO: 4). The real-time PCR reagent used herein was polymerase TAKARA Taq HS manufactured by Takara Bio Inc. Real-time PCR was performed with the addition of SYBR Green I (Lonza) diluted at a final concentration of 1/20000. The reaction was incubated using a Light Cycler 96 System (Roche) at 98° C./1 minute, followed by 50 PCR cycles of 98° C./10 seconds→60° C./10 seconds→72° C./10 seconds. The nucleic acid amplification reaction was monitored.

Example 32

<Method>

A viscous mixture, which was prepared by adding porcine-derived mucin to a culture suspension of *M. bovis* (BCG strain) ($1.0 \times 10^4$ CFU/mL) to result in a concentration of 20% by weight, was used as specimen A (artificial sputum).

Aqueous solutions having Compositions 11 to 15 listed below were used as specimen treatment reagents. In Table 3, each composition is in the form of an aqueous solution, and the proportion of each component in the aqueous solution is expressed in percent (%) by weight.

In a container, 5 mL of each specimen treatment reagent was added to 3 mL of the specimen A. The container was shaken 10 times vertically for mixing such that a liquid mixture was formed, and the liquid mixture was allowed to stand still at room temperature for 5 minutes. Thereafter, the total volume of the liquid mixture was allowed to permeate through a carrier for adsorbing a nucleic acid (silica monolith). Then, 15 mL of a 40% ethanol aqueous solution (serving as a washing liquid) was allowed to permeate through the carrier for washing. After the washing, 200 µL of sterile distilled water (serving as an eluent) was allowed to permeate through the carrier. Then, a liquid containing nucleic acids that permeated through the carrier was collected. The nucleic acid-containing liquid was used as a sample, followed by amplification and detection by real-time PCR.

TABLE 3

| | Treatment reagent composition |
|---|---|
| Composition 11 | 5% NaOH + 5% NALC + 60% EtOH |
| Composition 12 | 5% KOH + 5% NALC + 60% EtOH |
| Composition 13 | 5% NaOH + 5% L-cyteine + 60% EtOH |
| Composition 14 | 5% NaOH + 5% L-cyteine ethyl ester hydrochloride + 60% EtOH |
| Composition 15 | 5% NaOH + 5% L-cyteine methyl ester hydrochloride + 60% EtOH |

<Results>

In the case of using any of the treatment reagents of Compositions 11 to 15, specific amplification of a target *M. bovis*-derived nucleic acid was observed. It was therefore confirmed that each of the treatment reagents of Compositions 11 to 15 has properties required for a treatment reagent.

The table below lists relative values of Ct values each reflecting the amount of collected nucleic acids obtained by real-time PCR. A Ct value represents the number of cycles of real-time PCR at a point where an amplification curve reaches a predetermined threshold of the amount of an amplification product. As the Ct value decreases, the amount of collected nucleic acids increases. In this Example, each Ct value is expressed as a value relative to a Ct value obtained in the test using the specimen treatment reagent of Composition 11, which is herein designated as 1.0.

TABLE 4

| | Ct value (relative value) |
|---|---|
| Composition 11 | 1.0 |
| Composition 12 | 1.0 |
| Composition 13 | 1.1 |
| Composition 14 | 1.1 |
| Composition 15 | 1.1 |

The amount of collected nucleic acids was equivalent between the tests using the specimen treatment reagents of Compositions 11 and 12. In addition, this amount of collected nucleic acids was confirmed to be greater than the amount of collected nucleic acids in each of the tests using the specimen treatment reagents of Compositions 13, 14, and 15.

Example 33

<Method>

A culture suspension of *M. bovis* (BCG strain) ($1.0\times10^4$ CFU/mL) was used as specimen B.

Aqueous solutions having Compositions 21 to 23 listed below were used as specimen treatment reagents. In Table 4, each composition is in the form of an aqueous solution, and the proportion of each component in the aqueous solution is expressed in percent (%) by weight.

In a container, 5 mL of each specimen treatment reagent was added to 3 mL of the specimen B. The container was shaken 10 times vertically for mixing such that a liquid mixture was formed, and the liquid mixture was allowed to stand still at room temperature for 5 minutes. Then, 100 μL of the liquid mixture was collected. DNA was collected in accordance with the procedures of usual ethanol precipitation and used as a sample, followed by amplification and detection by real-time PCR.

TABLE 5

| | Treatment reagent composition |
|---|---|
| Composition 21 | 5% NaOH + 5% NALC + 60% EtOH |
| Composition 22 | 5% NALC + 60% EtOH |
| Composition 23 | 5% NaOH + 5% NALC |

<Results>

In the case of using any of the treatment reagents of Compositions 21 to 23, specific amplification of a target *M. bovis*-derived nucleic acid was observed. It was therefore confirmed that each of the treatment reagents of Compositions 21 to 23 had ability to cause a nucleic acid to be released from a microorganism.

The table below lists Ct values each reflecting the amount of collected nucleic acids obtained by real-time PCR. It was confirmed that the largest amount of collected nucleic acids was obtained in the test using the specimen treatment reagent of Composition 21, and the second largest amount of collected nucleic acids was obtained in the test using the specimen treatment reagent of Composition 23.

TABLE 6

| | Ct value |
|---|---|
| Composition 21 | 26.8 |
| Composition 22 | 30.9 |
| Composition 23 | 28.5 |

Example 34

<Method>

An aqueous solution containing an *M. smegmatis*-derived purified nucleic acid at a concentration of 0.3 ng/μL was used as specimen C.

Aqueous solutions having Compositions 21 to 23 were used as specimen treatment reagents as in the case of Example 33.

In a container, 5 mL of each specimen treatment reagent was added to 3 mL of the specimen A. The container was shaken 10 times vertically for mixing such that a liquid mixture was formed, and the liquid mixture was allowed to stand still at room temperature for 5 minutes. Thereafter, the total volume of the liquid mixture was allowed to permeate through a carrier for adsorbing a nucleic acid (silica monolith). Then, 15 mL of a 40% ethanol aqueous solution (serving as a washing liquid) was allowed to permeate through the carrier for washing. After the washing, 200 μL of sterile distilled water (serving as an eluent) was allowed to permeate through the carrier. Then, a liquid containing nucleic acids that permeated through the carrier was collected. The nucleic acid-containing liquid was used as a sample, followed by amplification and detection by real-time PCR in the same manner as in Example 1.

<Results>

The table below lists Ct values each reflecting the amount of collected nucleic acids obtained by real-time PCR. In the case of using any of the treatment reagents of Compositions 21 to 23, specific amplification of a target *M. bovis*-derived nucleic acid was observed. It was therefore confirmed that each of the treatment reagents of Compositions 21 to 23 had ability to cause the carrier to adsorb nucleic acids. The amount of collected nucleic acids in the test using the specimen treatment reagent of Composition 21 was about 100- to 1000-fold greater than the amount of collected nucleic acids in the test using the specimen treatment reagent of either Composition 22 or 23, showing an obvious difference therebetween.

TABLE 7

| | Ct value |
|---|---|
| Composition 21 | 18.7 |
| Composition 22 | 24.9 |
| Composition 23 | 25.4 |

Example 35

<Method>

A viscous mixture, which was prepared by adding porcine-derived mucin to water to result in a concentration of 20% by weight, was used as specimen D (artificial sputum).

Aqueous solutions having Compositions 31 to 38 listed below were used as specimen treatment reagents. In Table 5, each composition is in the form of an aqueous solution, and the proportion of each component in the aqueous solution is expressed in percent (%) by weight.

In a container, 1 mL of each specimen treatment reagent was added to 1 mL of the specimen D. The container was strongly shaken for mixing such that a liquid mixture was formed, and the liquid mixture was allowed to stand still at room temperature for 5 minutes. Thereafter, fluidity of the liquid mixture was evaluated.

Fluidity was evaluated by measuring the migration length of 20 μL of each liquid mixture added dropwise to a 45-degree tilted glass plate having a smooth surface for 60 seconds. The measured migration lengths were compared, provided that each migration length is expressed as a value relative to a migration length for the liquid mixture obtained using the treatment reagent of Composition 38, which is herein designated as 1.0.

TABLE 8

| | Treatment reagent composition | Fluidity evaluation* | Relative value |
|---|---|---|---|
| Composition 31 | 5% NaOH + 5% NALC + 60% EtOH | A | 3.2 |
| Composition 32 | 5% NALC + 60% EtOH | D | 1.0 |
| Composition 33 | 5% NaOH + 5% NALC | A | 3.2 |
| Composition 34 | 5% NaOH + 60% EtOH | B | 2.6 |
| Composition 35 | 5% NALC | C | 2.0 |
| Composition 36 | 5% NaOH | B | 2.8 |
| Composition 37 | 60% EtOH | C | 1.6 |
| Composition 38 | Water | D | 1.0 |

*D ≤1.0, 1.0 < C ≤ 2.0, 2.0 < B ≤ 3.0, 3.0 < A

<Results>

The above table shows the results. It was confirmed that the mixtures obtained by using the specimen treatment reagents of Compositions 31 and 33 achieved the highest fluidity.

REFERENCE SIGNS LIST

S: specimen, 100: treatment reagent-accommodating container, 101: treatment reagent, 102: discharge opening, 10: pressure-feeding unit, 104: cover, 110: inner container space, 200: nucleic acid-collecting member, 203: accommodation space, 204: treatment reagent-supplying opening, 205: carrier that adsorbs a nucleic acid, 206: mixture-discharging opening, 420: mixing space, 421: mixture All publications, patents, and patent applications cited herein are incorporated herein by reference in their entirety.

The invention claimed is:

1. A specimen treatment reagent, comprising:
0.5 to 15% by weight of at least one thiol reductant selected from the group consisting of N-acetyl-L-cysteine, L-cysteine, L-cysteine ethyl ester, L-cysteine methyl ester, N-ethyl-L-cysteine, N-methyl-L-cysteine, and salts of these compounds;
more than 3.0% by weight to 20% by weight of at least one alkaline substance selected from the group consisting of sodium hydroxide and potassium hydroxide; and
20 to 80% by weight of ethanol,
wherein the specimen treatment reagent releases a nucleic acid from a specimen.

2. The specimen treatment reagent according to claim 1, wherein the thiol reductant is N-acetyl-L-cysteine or a salt thereof.

3. The specimen treatment reagent according to claim 1, further comprising a component that facilitates a carrier to adsorb the nucleic acid, wherein the component is at least one selected from the group consisting of a chaotropic agent and an organic solvent.

4. A method for separating a nucleic acid from a specimen, the method comprising adsorbing the nucleic acid separated from the specimen on a carrier containing silica in the presence of a mixture of the specimen treatment reagent according to claim 1 and the specimen,
wherein the specimen comprises the nucleic acid and a component crosslinked by an S—S bond.

* * * * *

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial
<220> FEATURE:
<223> OTHER INFORMATION: primer

<400> SEQUENCE: 1
acatgcaagt cgaacggaaa                                                20

<210> SEQ ID NO 2
<211> LENGTH: 20
<212> TYPE: DNA
<213> ORGANISM: Artificial
<220> FEATURE:
```

```
<223> OTHER INFORMATION: primer

<400> SEQUENCE: 2
cccaccaaca agctgatagg                                              20

<210> SEQ ID NO 3
<211> LENGTH: 20
<212> TYPE: DNA
<213> ORGANISM: Artificial
<220> FEATURE:
<223> OTHER INFORMATION: primer

<400> SEQUENCE: 3
acctcaccta tgtgtcgacc                                              20

<210> SEQ ID NO 4
<211> LENGTH: 22
<212> TYPE: DNA
<213> ORGANISM: Artificial
<220> FEATURE:
<223> OTHER INFORMATION: primer

<400> SEQUENCE: 4
aacgtctttc aggtcgagta cg                                           22

<210> SEQ ID NO 5
<211> LENGTH: 25
<212> TYPE: DNA
<213> ORGANISM: Artificial
<220> FEATURE:
<223> OTHER INFORMATION: primer

<400> SEQUENCE: 5
ggaagaagct tgcttctttg ctgac                                        25

<210> SEQ ID NO 6
<211> LENGTH: 26
<212> TYPE: DNA
<213> ORGANISM: Artificial
<220> FEATURE:
<223> OTHER INFORMATION: primer

<400> SEQUENCE: 6
agcccgggga tttcacatct gactta                                       26

<210> SEQ ID NO 7
<211> LENGTH: 23
<212> TYPE: DNA
<213> ORGANISM: Artificial
<220> FEATURE:
<223> OTHER INFORMATION: primer

<400> SEQUENCE: 7
gctccactac aagatggacc tgc                                          23

<210> SEQ ID NO 8
<211> LENGTH: 23
<212> TYPE: DNA
<213> ORGANISM: Artificial
<220> FEATURE:
<223> OTHER INFORMATION: primer

<400> SEQUENCE: 8
taggagtctg ggccgtgtct cag                                          23
```